US009101766B2

(12) United States Patent
Nekhendzy

(10) Patent No.: US 9,101,766 B2
(45) Date of Patent: Aug. 11, 2015

(54) ELICITING ANALGESIA BY TRANSCRANIAL ELECTRICAL STIMULATION

(75) Inventor: Vladimir Nekhendzy, Palo Alto, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 555 days.

(21) Appl. No.: 12/906,853

(22) Filed: Oct. 18, 2010

(65) Prior Publication Data

US 2011/0093033 A1 Apr. 21, 2011

Related U.S. Application Data

(60) Provisional application No. 61/252,452, filed on Oct. 16, 2009.

(51) Int. Cl.
*A61N 1/18* (2006.01)
*A61N 1/36* (2006.01)

(52) U.S. Cl.
CPC ........ *A61N 1/36017* (2013.01); *A61N 1/36021* (2013.01); *A61N 1/36014* (2013.01)

(58) Field of Classification Search
USPC ...................................... 607/45–46
See application file for complete search history.

(56) References Cited

U.S. PATENT DOCUMENTS 3,835,833 A 9/1974 Limoge
6,567,702 B1 5/2003 Nekhendzy et al.

OTHER PUBLICATIONS

Nekhendzy V, Fender CP, Davies MF, et al., "The Role of the Craniospinal Nerves in Mediating the Antinociceptive Effect of Transcranial Electrostimulation in the Rat", Anesth Analg 2006;102:1775-80.*
Dougherty et al., "Trans-Cranial Electrical Stimulation Attenuates the Severity of Naloxone-Precipitated Morphine Withdrawal in Rats", "Life Sciences", 1989, pp. 2051-2056, vol. 44, Publisher: Pergamon Press, Published in: U.S.A.
Stanley et al., "Transcutaneous Cranial Electrical Stimulation Increases the Potency of Nitrous Oxide in Humans", "Anesthesiology", Oct. 1982, pp. 293-297, vol. 57, No. 4, Publisher: The American Society if Anesthesiologist, Inc, Published in: U.S.A.
Becser, N. et al., "Extracranial nerves in the posterior part of the head: anatomic variations and their possible clinical significance", "Spine", 1998, pp. 1435-1441, vol. 23, Publisher: Lippincott-Raven Publishers, Published in: http://journals.lww.com/spinejournal/pages/articleviewer.aspx?year=1998&issue=07010&article=00001&type=abstract.

(Continued)

*Primary Examiner* — Brian T Gedeon
(74) *Attorney, Agent, or Firm* — Beusse Wolter Sanks & Maire PLLC; Eugene J. Molinelli

(57) ABSTRACT

The inventions include a method of eliciting analgesia in a human subject by Transcranial Electrical Stimulation (TCES, herein "TES"). Electrodes secured to the skin of the subject's head at particular sites provide an electrical current that includes a direct current combined with rectangular AC current pulses delivered at a particular frequency of between 10 and 100 Hz. In an embodiment the total current transmitted, a sum of the DC component and a Mean Absolute Deviation (MAD) of the current pulses, has a value between 0.2 and 20 mA. The method is used to produce analgesia during perioperative period, surgery and the post-operative procedure. It can also be used for treating acute chronic pain and a wide variety of other conditions.

21 Claims, 11 Drawing Sheets

(56) References Cited

OTHER PUBLICATIONS

Benarroch E. E., et al., "Pain-autonomic interactions: a selective review", "Clinical Autonomic Research", 2001, pp. 343-349, vol. 11, Publisher: Lippincott Williams & Wilkins, Published in: http://link.springer.com/article/10.1007%2FBF02292765.

Klawansky S., et al., "Meta-analsysis of randomized controlled trials of cranial electrostimulation efficacy in treating selected psychological and psychological conditions", "The Journal of Nervous and Mental Disorders", 1995, pp. 478-484, vol. 183, No. 7, Publisher: Williams & Wilkins, Published in: http://journals.lww.com/jonmd/Abstract/1995/07000/Meta_Analysis_of_Randomized_Controlled_Trials_of.10.aspx.

Lebedev, V.P., et al., "Devices for noninvasive transcranial electrostimulation of the brain endorphinergic system: application for improvement of human psycho-physiological status", "Artificial Organs", 2002, pp. 248-251, vol. 26, No. 3, Publisher: International Society for Artificial Organs and Transplantation and Wiley Periodicals, Inc., Published in: http://onlinelibrary.wiley.com/doi/10.1046/j.1525-1594.2002.06944.x/abstract.

Limoge A., et al., "Transcutaneous cranial electrical stimulation (TCES): a review", "Neuroscience and Biobehavioral Reviews", 1999, pp. 529-538, vol. 23, No. 4, Publisher: Elsevier B.V., Published in: http://www.sciencedirect.com/science/article/pii/S0149763498000487.

Pinosky M.L., et al., "The effect of bupivacaine skull block on the hemodynamic response to craniotomy", "Anesthesia and Analgelsia", 1996, pp. 1256-1261, vol. 83, Publisher: IARS, Published in: http://www.anesthesia-analgesia.org/content/83/6/1256.long.

Piovesan E.J., et al., "Referred pain after painful stimulation of the greater occipital nerve in humans: evidence of convergence of cervical afferences on trigeminal nuclei", "Cephalalgia", 2001, pp. 107-109, vol. 21, No. 2, Publisher: Blackwell Publishing, Published in: http://onlinelibrary.wiley.com/doi/10.1046/j.1468-2982.2001.00166.x/abstract;jsessionid=0662EC8C37115FBBF1269C121F7228AB.d01t02.

Sessle B.J., et al., "Convergence of cutaneous, tooth pulp, visceral, neck and muscle afferents onto nociceptive and non-nociceptive neurones in trigeminal subnucleus caudalis (medullory dorsal horn) and its implications for referred pain", "Pain", 1986, pp. 219-235, vol. 27, No. 2, Publisher: Elsevier, Published in: http://www.painjournalonline.com/issues.

Tubbs R. S., et al., "Landmarks for the identification of the cutaneous nerves of the occipital and nuchal regions", "Clinical Anatomy", 2007, pp. 235-238, vol. 20, No. 3, Publisher: Wiley-Liss Inc., Published in: http://onlinelibrary.wiley.com/doi/10.1002/ca.20297/abstract.

Urasaki E., et al., "Effect of transcutaneous electrical nerve stimulation (TENS) on central nervous system amplificaiton of somatosensory input", "Journal of Neurology", 1998, pp. 143-148, vol. 245, Publisher: European Neurological Society, Published in: http://www.researchgate.net/publication/51342491_Effect_of_transcutaneous_electrical_nerve_stimulation(TENS)_on_central_nervous_system_amplification_.

Kano, T., et al., "The Role of the Somatosensory System in General Electroanesthesia", "Anesthesia & Analgesia", 1974, pp. 667-671, vol. 53, No. 5, Publisher: IARS, Published in: http://www.anesthesia-analgesia.org/content/53/5/667.full.pdf+html.

Kano, T., et al., "Electroanesthesia (EA) Studies: EA Produced by Stimulation of Sensory Nerves of the Scalp in Rhesus Monkeys", "Anesthesia & Analgesia", 1976, pp. 536-541, vol. 55, No. 4, Publisher: IARS, Published in: http://www.anesthesia-analgesia.org/content/55/4/536.full.pdf+html.

Nekhendzy, V., et al., "The Antinociceptive Effect of Transcranial Electrostimulation with Combined Direct and Alternating Current in Freely Moving Rats", "Anesthesia & Analgesia", 2004, pp. 730-737, vol. 98, No. 3, Publisher: IARS, Published in: http://www.anesthesia-analgesia.org/content/98/3/730.full.pdf+html.

Nekhendzy, V., et al., "The Role of the Craniospinal Nerves in Mediating the Antinociceptive Effect of Transcranial Electrostimulation in the Rat", "Anesthesia & Analgesia", 2006, pp. 1775-1780, vol. 102, No. 6, Publisher: IARS, Published in: http://www.anesthesia-analgesia.org/content/102/6/1775.full.pdf+html.

* cited by examiner

FIG. 3 TES Electrode Placement

FIG. 4    TES Electrode Placement

ELICITING ANALGESIA BY TRANSCRANIAL ELECTRICAL STIMULATION

CROSS REFERENCE TO RELATED APPLICATIONS

This application claims benefit of Provisional Application 61/252,452, filed on Oct. 16, 2009, incorporated herein by reference, under 35 U.S.C. §119(e).]

STATEMENT OF GOVERNMENTAL INTEREST

This invention was made without government funding.

FIELD OF THE INVENTION

This invention relates generally to generating analgesic effects by Transcranial Electrical Stimulation (TES). More particularly, it relates to specific operating conditions for TES.

BACKGROUND

Neuromodulation has been variously defined as a) the science of how electrical, chemical, and mechanical interventions can modulate or change central and peripheral nervous system functioning; b) the form of therapy in which neurophysiological signals are initiated or influenced with the intention of altering the function and performance of the nervous system and achieving therapeutic effects, or c) the therapeutic alteration of activity in the central, peripheral or autonomic nervous systems, electrically or pharmacologically, by means of implanted devices. Implantable devices, however, carry a certain risk of surgical complications (e.g. infection, scarring), are limited by the current that can be used for therapeutic purposes, and dictate the need to avoid the electromagnetic and electrical fields that may interfere with function of the device.

Transcranial electrostimulation (TES) is a collective term for a variety of noninvasive electrotherapeutic techniques where electrical current is administered through electrodes positioned on the skin of the subject's head. TES has been reported to produce a plethora of non-pharmacological, natural therapeutic effects, including analgesia, anxiolysis and stress reduction, enhancement of mood and cognition, positive effects in patients with neurodegenerative diseases and impaired neurological function, alleviation of symptoms of drug, alcohol and nicotine withdrawal, stimulation of immune system, acceleration of regeneration and tissue repair, and other.

The use of electrical currents for the purpose of producing narcosis or analgesia was pioneered by the French physiologist Leduc nearly 100 years ago. Over the next 70 years, several attempts were made to produce and maintain a state of general anesthesia by administering different parameters of electrical currents, applied to the skin of the subject's head (i.e., transcranially and transcutaneously). However, due to the high intensity of current required to induce general anesthesia, these efforts were abandoned and superseded by attempts to produce analgesia, rather than general anesthesia, by application of electrical currents. TES is decidedly different from transcutaneous electrical nerve stimulation (TENS), which applies electrical stimulation in the vicinity of the peripheral nerve(s) supplying the affected area in an attempt to provide pain relief to that area through activation of the low-threshold mechanoreceptive Aβ-fibers, which "close the gate" to the painful stimuli entering the spinal cord, as opposed to a systemic analgesia obtainable using TES. TES should also not be confused with another from of TENS called PENS (percutaneous electric nerve stimulation, sometimes also called PNT, percutaneous neuromodulation therapy), where the skin is pierced by electrodes.

Different types of Transcranial Electrical Stimulation (TCES, herein ("TES")) are suggested in the literature under a wide variety of names, including Limoge current, Lebedev current, Cranial Electrotherapy Stimulation (CES), Low Current Electrostimulation, Auricular Microstimulation, and others [Limoge, 1999].

There is still a need for improved TES methods to treat or prevent pain and other various medical conditions.

SUMMARY OF THE INVENTION

Certain embodiments of the invention are directed to a method for administering transcranial electrical stimulation (TES) for treating or preventing a medical condition in a human subject, that includes a) removably fixing a first frontal electrode and a pair of second electrodes to the skin of the subject's head; and b) supplying electrical current to the first electrode and to the pair of second electrodes for a period of time to elicit a response from the subject, wherein 1. the electrical current comprises AC current pulses superimposed on direct current, AC current pulses alone or DC current alone, and 2. the AC current pulses are supplied at a particular frequency of between from about 10 Hz and from about 100 Hz. The total current value supplied can range from about 0.2 mA and about 20 mA, and the duration of the TES procedure is typically 10 to 60 minutes. In certain embodiments the current pulses range from about 3.5 to about 8 ms in duration, which duration can be changed during TES. In another embodiment the particular frequency of electric current is changed during the TES procedure. The AC current pulses can have any waveform, and in an embodiment the waveform is changed during TES.

When AC current pulses are used, they can be either unipolar or bipolar, and in an embodiment the polarity can be changed during TES. In certain embodiments the AC current pulses include high frequency AC current pulses of from about 1 kHz to about 10 MHz that can have any waveform. In an embodiment where the electric current is AC current pulses superimposed on DC current, a ratio between the value of the direct current and the Mean Absolute Deviation (MAD) value of the current pulses is between from about 5:1 and from about 1:1, preferably about 2:1.

The position of the electrodes on the subject's head can vary. In an embodiment the first frontal electrode is removably fixed to the skin of the subject's forehead above the eyebrows and the pair of second electrodes is removably fixed to the skin in the retromastoid area.

Medical conditions that can be treated or prevented using the new TES methods include acute and chronic pain conditions and syndromes; immune system dysfunction and disorders; decreased wound healing; tissue and nerve regeneration disorders (herein including accelerating normal tissue and nerve healing and regeneration); impaired neurological function (herein including facilitation of neurorehabilitation of patients suffering from stroke, traumatic brain and spinal cord injury, and seizure disorder); and drug dependence and withdrawal (herein including the use, misuse, abuse, dependence and withdrawal from any prescription drug or illegal drug, including pain killers, psychoactive drugs, opiates, alcohol, and nicotine) for which the preferred particular frequency is from about 30 to 65 Hz, preferably 60 Hz, although any frequency from 10 to 100 Hz can be used. Other medical conditions include attention deficit disorder, anxiety, depression, mood and sleep disturbances, post-traumatic stress disorder, appetite disturbances, Alzheimer's disease, neurodegenerative diseases including Parkinson's disease, sexual dysfunction, fatigue, combat stress, and improving neurocognitive and mood states and performance, for which the preferred particular frequency is between from about 60 Hz and from about 100 Hz, preferably 100 Hz.

Our clinical experience has also shown accelerated healing of facial abrasions and acne under the influence of TES. TES has been demonstrated to provide functional improvement in patients suffering from stroke, traumatic brain and spinal cord injury, seizures (especially through stimulation of trigeminal nerve and a variety of neurodegenerative diseases (e.g. Parkinson's disease, Alzheimer's disease).

BRIEF DESCRIPTION OF THE DRAWINGS

FIG. 8 shows an example of single bipolar (bidirectional) AC pulses that have a DC component.

DETAILED DESCRIPTION

Figure 1:
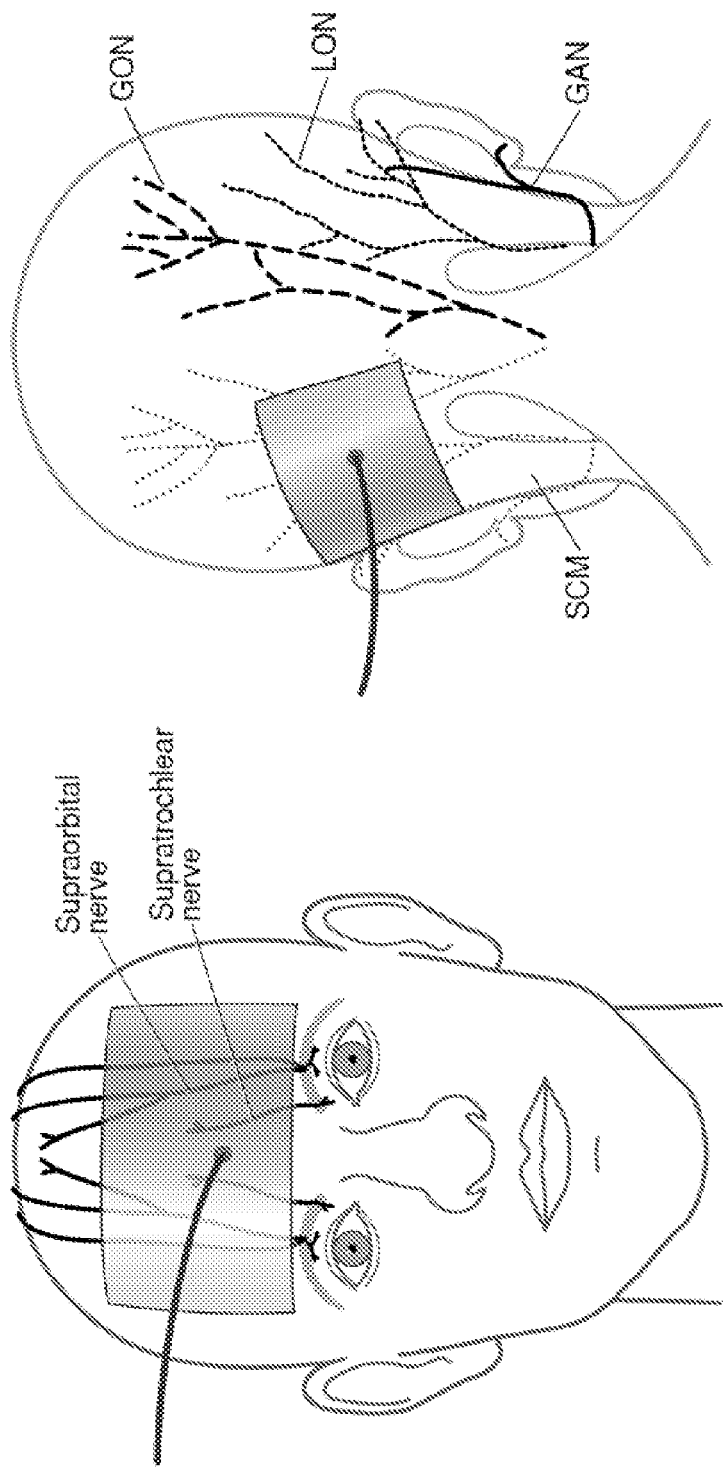
FIG. 1 shows the positioning of the frontal (on left) and posterior (on right) TES electrodes over the projections of the peripheral craniospinal nerves. SCM—Sternocleidomastoid muscle. GON—greater occipital nerve, LON—lesser occipital nerve, and GAN—Greater auricular nerve.

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

The invention provides various methods for administering TES to treat or prevent acute and chronic pain, cognitive and mood conditions and disorders, and a variety of other medical conditions to a subject in need of treatment. An embodiment of the invention includes a) removably fixing a first frontal electrode and a pair of second electrodes to the skin of the subject's head; and b) supplying electrical current to the first electrode and to the pair of second electrodes for a period of time to elicit a response from the subject, wherein 1. the electrical current comprises AC current pulses superimposed on direct current, AC current pulses alone or DC current alone, and 2. the current pulses are supplied at a particular frequency of between from about 10 Hz and from about 100 Hz. The total current value supplied can range from about 0.2 mA and about 20 mA, and the duration of the TES procedure is typically 10 to 60 minutes. In certain embodiments the current pulses are below approximately 8 msec, preferably about 3.5 msec, which duration can be changed during TES. In another embodiment the particular frequency of electric current is changed during the TES procedure. The AC current pulses can have any waveform, and in an embodiment the waveform is changed during TES.

When AC current pulses are used, they can be either unipolar or bipolar, and in an embodiment the polarity of stimulation can be changed during TES. In certain embodiments the AC current pulses include high frequency AC current pulses of from about 1 kHz to about 10 MHz that can have any waveform. In an embodiment where the electric current is AC current pulses superimposed on DC current, a ratio between the value of the direct current and the Mean Absolute Deviation (MAD) value of the current pulses is between from about 5:1 and from about 1:1, preferably about 2:1.

The position of the electrodes on the subject's head can vary. In an embodiment the first frontal electrode is removably fixed to the skin of the subject's forehead above the eyebrows and the pair of second electrodes is removably fixed to the skin in the retromastoid area.

Medical conditions that can be treated or prevented using the new TES methods include acute and chronic pain conditions and syndromes; immune system dysfunction and disorders; decreased wound healing; tissue and nerve regeneration disorders (herein including accelerating normal tissue and nerve healing and regeneration); impaired neurological function (herein including facilitation of neurorehabilitation of patients suffering from stroke, traumatic brain and spinal cord injury, and seizure disorder); and drug dependence and withdrawal (herein including the use, misuse, abuse, dependence and withdrawal from any prescription drug or illegal drug, including pain killers, psychoactive drugs, opiates, alcohol, nicotine and nicotine) for which the preferred particular frequency is from about 30 to 65 Hz, preferably 60 Hz, although any frequency from 10 to 100 Hz can be used. Other medical conditions include attention deficit disorder, anxiety, depression, mood and sleep disturbances, post-traumatic stress disorder, appetite disturbances, Alzheimer's disease, neurodegenerative diseases including Parkinson's disease, sexual dysfunction, fatigue, and combat stress, for which the preferred particular frequency is between from about 60 Hz and from about 100 Hz, preferably 100 Hz. The new TES methods can also be used to improving neurocognitive and mood states and performance in both subjects having a related medical condition and in normal subjects, for which the preferred particular frequency is also between from about 60 Hz and from about 100 Hz, preferably 100 Hz.

With reference to the corresponding preferred particular frequencies. It is important to note that the optimal frequency for the present TES methods varies with the individual subject and condition or combination of conditions that a subject may have.

Earlier TES techniques that claimed effectiveness in treating pain and other medical conditions and disorders in humans (e.g. Limoge or Lebedev current) were developed from the experiments where the skin electrode positioning was not utilized; the subcutaneous needle electrodes or bone-affixed electrodes were used instead. Limoge currents consisted of high frequency (166 kHz) intermittent bursts of bidirectionally balanced current "packed" into trains. The current was applied transcranially and transcutaneously at 100 kHz for 4 msec to 6 msec intervals. U.S. Pat. No. 3,835, 833. TES with Limoge current has been used as part of an anesthetic management in a wide variety of surgical cases. It has also been shown to: increase the potency of nitrous oxide in humans by 30-40% [Stanley, 1982A]; reduce the need for opiates during neuroleptanesthesia by 50-80% [Stanley, 1982B]; potentiate opioid-induced analgesia in rats [Dougherty, 1989]; and decrease minimum alveolar concentration (MAC) of halothane in rats [Mantz, 1992].

Lebedev current in its original description did utilize a combination of DC and AC currents, but the AC was administered at a very specific and narrow frequency range (77-78 Hz). It was successfully used in different types of surgery, including cardiothoracic procedures, and in different age groups, including pediatrics [Katsnelson, 1987, 1989; Kartavkin, 1987; Zamiatnina, 1987], [Lebedev, 1989]; as well as in patients suffering from chronic pain [Skorometz, 1987; Akimov, 1987; Gurchin, 1987; Kasimova, 1987]. In its current application, Lebedev current involves the administration of AC only.

We now know that cutaneous craniospinal nerves play a critical role in producing analgesia in primates. (Kano T, et al. Anesth Analg 1974; 53:667-71; Kano T, et al. Anesth Analg 1976; 55:536-41; Nekhendzy V et al., Anesth Analg 2006; 102:1775-80). Our laboratory developed a clinically-relevant rat model of cutaneously-administered TES, where electrodes were positioned on the rat's head in exactly the same anatomical locations as were later used in humans. U.S. Pat. No. 6,567,702. Using this rat model, the primary role of the cutaneous craniospinal nerves in mediating the TES-induced electrotherapeutic effects was confirmed, and certain frequency-response parameters that consistently produced analgesia (called antinociception in animals) were identified.

Thus, the Limoge and Lebedev TES, which were developed without taking into account the paramount role of cutaneous craniospinal nerves in mediating TES electrotherapeutic action, may be considered suboptimal.

In the TES methods described in U.S. Pat. No. 6,567,702, it was necessary to periodically change the frequency of electric stimulation at intervals of between approximately 5 minutes and approximately 60 minutes during TES treatment to achieve analgesia in the subject. It has now been discovered that it is not necessary to periodically change the frequency of electric stimulation during treatment to treat or prevent acute and chronic pain and the other medical conditions listed herein, or to increase cognition or modulate mood in humans. In the present methods a current of a particular frequency can be used throughout the TES procedure.

Anatomical Basis for Positioning the Electrodes for TES
Proper TES Electrode Positioning is Essential for Producing Optimal Electrotherapeutic Effects.

TES electrodes are positioned on the skin on the subject's head and neck, which is innervated by cutaneous nerves. The $C_2$-$C_{3(4)}$ primary afferents and their corresponding DRG project directly, among other structures, to the $C_1$-$C_4$ segments of the upper cervical spinal cord (UCC), the lateral cervical nucleus (LCN), the nucleus of the tractus solitarius (NTS), and the dorso-lateral funiculus (DLF). The supraorbital nerves and the $V_1$ division of the trigeminal ganglion abundantly project to all parts of the brainstem trigeminal nuclear complex (the main sensory nucleus and all subdivisions of the spinal trigeminal nucleus, including subnucleus caudalis [Vc]), to the adjacent reticular formation, and to the NTS.

At the UCC level, the terminations overlap widely with the location of the cell bodies of the wide-dynamic range (WDR) and nociceptive-specific (NS) second-order neurons, which provide either the largest or substantial contribution to the ascending spinal pathways targeting the centers intimately involved in processing and modulation of the nociceptive input: the ventrobasal and posterior thalamus, the mesencephalon and the periaqueductal gray (PAG), the rostral ventromedial medulla (RVM) serotonergic neurons (nucleus raphe magnus and adjacent reticular formation), the medullary A5 and pontine A6-7 (locus coeruleus and subcoerulear) noradrenergic cell groups, the NTS, the parabrachial nucleus (PBN), different parts of the hypothalamus, ventrolateral medulla (VLM) (lateral reticular formation, $VLM_{lat}$ and dorsal reticular nucleus, $DR_t$), some telencephalic areas (septal nuclei, nucleus accumbens) and amygdala.

Because similar pathways to the above structures originate in the Vc and NTS second-order neurons, the UCC, Vc and NTS relays seem to be of utmost importance to the TES analgesic and other therapeutic actions, creating a framework for neuromodulating effect of TES on the ascending nociceptive and somatosensory inputs. PAG plays major role in modulation and integration of the nociceptive, behavioral somatic and autonomic responses; the NTS represents a major site for processing and integrating multiple visceral and somatic inputs and generating autonomic responses; the hypothalamus integrates the somatosensory, visceral and cognitive information with regulation (through the hypothalamic-pituitary-adrenal axis) of hormonal secretion and activity of the brain stem and spinal cord neurons that mediate autonomic responses; the septal nuclei, nucleus accumbens and especially amygdala are involved in expression of emotional responses and memory processes; the caudal brainstem reticular formation—subnucleus reticularis dorsalis (SRD) modulates spinal nociceptive transmission by means of diffuse noxious inhibitory controls (DNIC).

The described anatomical framework is also supported by functional physiological connections, that provide either direct or indirect (through local neuronal circuitry) functional coupling between the $C_2$-$C_{3(4)}$ and $V_1$ primary afferents and centrally-projecting UCC, Vc and NTS neurons. NTS neurons demonstrate excitatory convergence of sensory inputs from the cornea ($V_1$ receptive field) and brachial plexus (cervical afferents), and convergence of inputs from both the brachial plexus and dorsolateral PAG on single NTS neurons. This establishes one of the key roles of the NTS (and the NTS-PBN-PAG interaction) as a major interface for somatic afferent integration with descending inputs from the midbrain.

Without being bound by theory, it has been suggested based on electrophysiological evidence that TES may be a direct modulating influence on the centrally-projecting second-order neurons. Large numbers of the Vc and $VLM_{lat}$ neurons projecting to the hypothalamus display the cutaneous receptive fields corresponding to the distribution of the $V_1$ and $C_2$-$C_{3(4)}$ primary afferents. Given tight neuronal interconnections which exist both within Vc itself and between the Vc and other parts of the trigeminal nuclear complex, it is quite possible that other nociceptive and somatosensory pathways originating in the second-order Vc neurons may be equally engaged during the TES stimulation. TES may activate craniospinal nerves that in turn engage a wide range of the supraspinal structures that in turn, initiate descending inhibition of the spinal nociceptive input (i.e. analgesia) and trigger a variety of different electrotherapeutic neuromodulating responses, perhaps through increased release and turnover of serotonin, norepinephrine, dopamine and endogenous opioids observed during TES.

Other mechanisms that may be specific to the electrotherapeutic neuromodulating action of TES with direct current only (tDC) (an embodiment) may involve global modulation of central neuroplasticity and extensive neural networks, induced by a combination of hyper- and depolarizing effects of electrical current on neuronal axons and synaptic function.

Although the exact neurobiological substrate of TES action within the central nervous system remains uncertain, our research has established the pivotal role of TES-induced activation of cutaneous craniospinal nerves supplying the subject's head in triggering therapeutic responses to TES. We have demonstrated that the analgesic effect of TES is lost when cutaneous nerves supplying the skin under the electrodes are blocked with a local anesthetic. This shows that direct action of electrical current on the brain has a minor (if any) role in triggering therapeutic responses to TES. The neuroanatomical and physiological studies conducted over the last two decades described above have provided a detailed description of the central projections of the cutaneous nerves supplying the skin on the human head, offering an insight into the likely mechanism of the TES analgesic and neuromodulating action. (this relates to the projections to the CNS, not to the peripheral skin).

Figure 3:
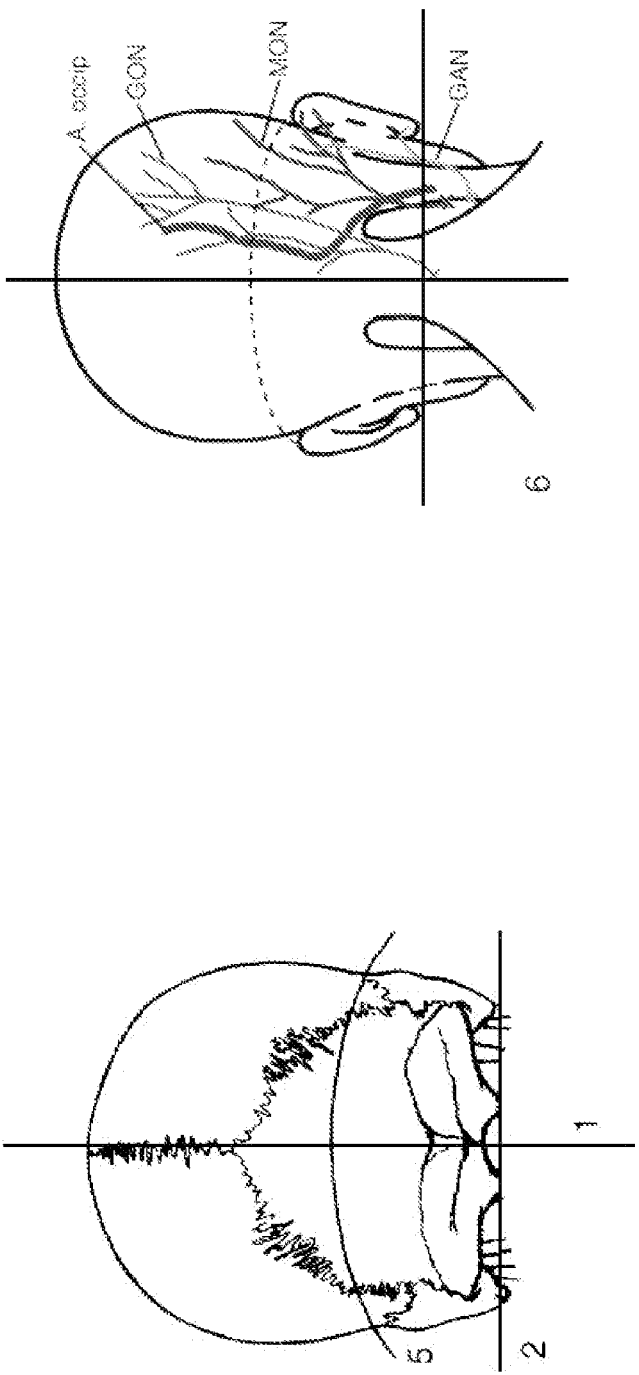
FIG. 3 Anatomical landmarks for identifying proper positioning of the TES occipital electrodes. Modified from Becser N et al.: Spine 1998; 23(13): 1435-1441. Legends on left: 1—Midline, 2—Intermastoid (IM) line: a transverse line between the caudal tips of the mastoid processes, 5—Superior nuchal line: the ridge of the attachment of the suboccipital muscles on the occipital bone, Legends on right: occip.—Occipital artery, GON—Greater occipital nerve, MON—Minor (lesser) occipital nerve (LON), GAN—Greater auricular nerve.
Figure 4:
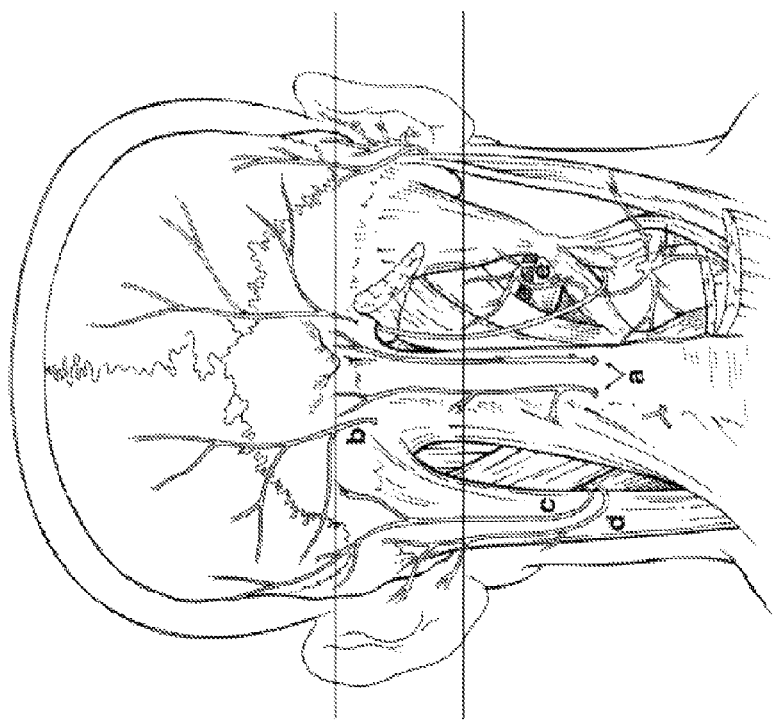
FIG. 4 Anatomical landmarks for identifying proper positioning of the TES occipital electrodes. Modified from Tubbs R S et al. Clinical Anatomy 2007; 20: 235-238. Legends: Superior line: most prominent point of external occipital protuberance (EOP), Inferior line: intermastoid (IM) line, a—Third occipital nerve, b—Left GON, c—Left LON, d—Mastoid branch of the GAN, e—Suboccipital nerve.

In an embodiment the frontal electrode is placed on the subject's forehead over the areas of cutaneous innervation supplied by the supraorbital and supratrochlear nerves as follows: inferiorly, approximately at the level of the eyebrows, and extending superiorly, approximately to the hair line, along the lateral part of the orbit. The electrode position can vary based on the response of the individual subject, the type of electrical stimulation being used and the medical condition being treated. See FIGS. 3-5.

Cutaneous innervation of the retromastoid area to which the pair of posterior electrodes are attached is provided by cutaneous branches of the greater occipital nerves (GON), lesser occipital nerves (LON) and greater auricular nerves (GAN). The frontal area of the head is innervated by cutaneous branches of the ophthalmic ($V_1$) division of the trigeminal nerve (supraorbital and supratrochlear nerves). The primary afferent fibers of these mixed sensory nerves originate in the $C_2$-$C_{3(4)}$ sensory cell bodies of the dorsal root ganglia (DRG) and the gasserian ganglion respectively, and show predominance of the Aδ- and C-fibers associated with the thermo- and nociceptive function over the low-threshold mechanoreceptive Aβ-fibers. The posterior pair of electrodes should be positioned to encompass the following approximate area, bordered by: outside—the mastoid process; inside—2 cm medial to the EOP; inferiorly—the IM line; superiorly—at least 1 cm above the EOP. See FIGS. 3-5.

Figure 5:
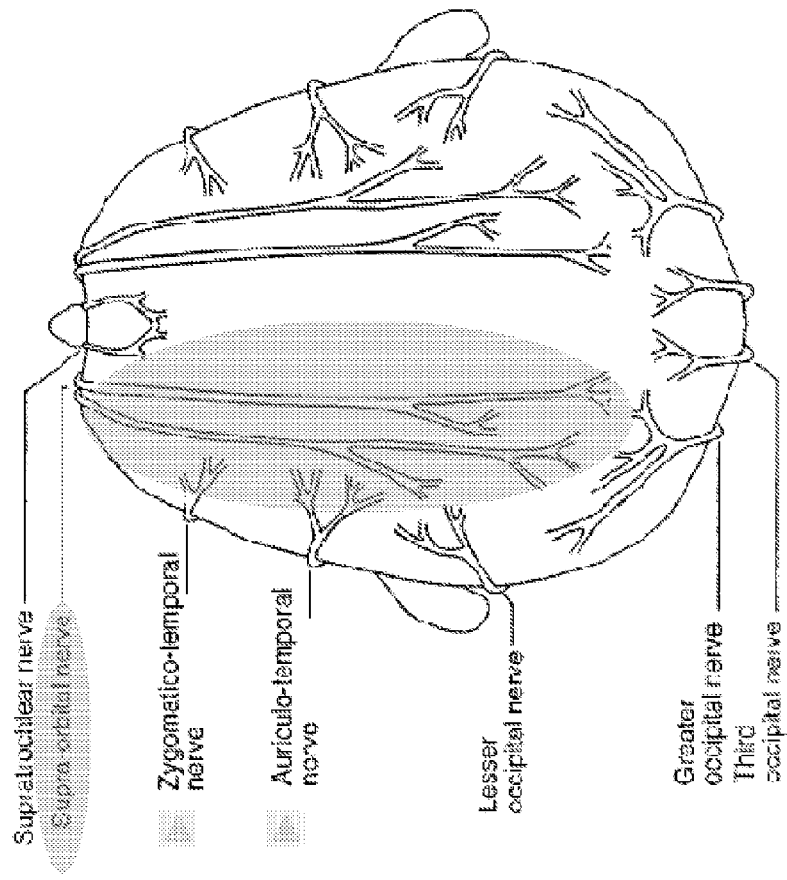
FIG. 5 Anatomical landmarks depicting the areas of other positioning of TES electrodes for stimulating the branches of the trigeminal, greater occipital and lesser occipital nerves. Modified from Pinosky M L et al. Anesth Analg 1996; 83: 1256-61. The supraorbital nerve is a branch of the first ($V_1$) division of the trigeminal nerve; the zygomaticotemporal nerve is the terminal branch of the second ($V_2$) division of the trigeminal nerve; the auriculotemporal nerve is the terminal branch of the mandibular nerve ($V_3$ division of the trigeminal nerve).

TES electrodes can also be placed over skin areas receiving continuous innervation by the GON, LON and trigeminal nerves (FIG. 5). For example, sensory input from the supraorbital nerve ($V_1$ division of the trigeminal nerve), the zygomaticotemporal ($V_2$ division of the trigeminal nerve) and the auriculotemporal nerve ($V_3$ division of the trigeminal nerve) will all converge in different, but tightly interconnected parts of the brain stem trigeminal nuclear complex, with anticipated subsequent activation of the second-order Vc neurons—one of the critical primary relays initiating the TES neuromodulating action. When positioning the TES electrodes over these other areas of the skull, targeting the electrode placement over the cutaneous areas overlaying the projections of the motor cortex, dorsolateral prefrontal cortex, occipital and somatosensory cortices may be preferred, as tDC application over these areas is associated with the variety of neuromodulating effects. In certain embodiments, the subject may respond better to DC current only that to either other option (AC rectangular current pulses superimposed on DC current, or AC pulses of different shape alone).

The sizes of the posterior and frontal electrodes are ideally configured individually for each patient to cover the described areas of cutaneous innervation, but should be probably not smaller than approximately 5×5 cm for each of the posterior electrodes, and 5×10 cm for the frontal electrode. If the electrodes are significantly smaller than this, the TES current density will be reduced and the risk of skin burns during TES administration will be greater. To assure appropriate coverage of the areas of cutaneous innervation under the electrodes, both frontal and posterior TES electrodes can each be represented by a single or multiple electrodes, a technique well known in the art.

The value of the AC current can be measured either in MAD or root-mean-square (RMS). While RMS may provide a more accurate representation of the overall "power" of the ac current, MAD measurement may be preferred because it is associated with delivering a higher spike value of ac current, which is important for stimulating peripheral nerve fibers and recruiting them in the subject's response to TES treatment.

Adjusting the Current Intensity and Duration

Electric current, a movement or flow of electrically charged particles, is typically measured in amperes. The intensity of the TES current is typically brought to the individual patient's tolerance level gradually, consistent with eliciting a strong, but comfortable sensation under the electrodes. This sensation typically indicates activation of the Aδ fibers of the primary cutaneous craniospinal afferent neurons. The intensity of the electrode current can also be adjusted up or down during TES administration according to the patient's comfort level, with the goal of maintaining the "strong, but comfortable" sensation for the longest period of time during the process of TES treatment. When well tolerated, the present methods for applying TES can be applied once or several times a day, depending on the individual patient, and/or as deemed necessary or desired by the operator and/or the patient.

In an embodiment the total current transmitted is between approximately 0.2 mA and approximately 20 mA. In another embodiment the ratio between the value of the direct current and the Mean Absolute Deviation (MAD) value of the current pulses is between approximately 5:1 and approximately 1:1, preferably approximately 2:1. As a guideline, the duration of each current pulse is typically below approximately 8 msec, preferably about 3.5 msec.

The techniques of the present invention can be implemented using a controllable waveform generator and suitable electrodes positioned on the forehead and on the upper part of the neck e.g., in the vicinity of the mastoid processes. The hardware for TES therapy using the present methods preferably includes conventional state-of-the-art components and circuitry. It will be apparent to one of average skill in the art, upon reading this disclosure, how to select and program suitable hardware. The duration of application of current to a patient may range from minutes to days, depending on the condition being treated or desired results. It may also follow a schedule in which the patient is treated for a predetermined period of time over successive days, or multiple times during the same day.

During TES current application, a particular pulse frequency within the preferred or effective range is maintained. In general, the optimal frequency value for treating a medical condition, for example treating pain by eliciting analgesia, depends upon the sensitivity and requirements of the subject and the condition being treated, and is therefore difficult to determine without at least some amount of experimentation. This value can be determined empirically before an extended course of TCES is initiated. For example, although a range of about 30-65 Hz, most preferably 60 Hz is preferred for treating pain, the response of any individual subject may vary, perhaps responding better to 50 Hz or 70 Hz. Due to subject variation, an embodiment includes adjusting the particular frequency up or down at any time during the procedure to scan the frequencies within the effective range in order to find the frequency that elicits the optimal response from the subject. For example the subject's response to the particular frequency may drop off or fall below acceptable levels. In this case, the operator may scan the frequencies to try to identify a different particular frequency to which the subject has a more robust response.

In some embodiments the frequency is changed, while other parameters are held constant, so that only the time between pulses is shortened or extended. However, in some embodiments one or more of the following are changed either independently of or together with changing the particular frequency: waveform of the AC current, the intensity of the current, and the duration of pulses and directionality (unipolar/bipolar). Preferably, the pulse duration is held constant even when the particular pulse frequency changes. Pulse duration is typically below 8 msec, more preferably from approximately 3.5 msec to about 8 msec. The ideal frequency for a particular patient can be determined empirically before an extended course of TES is initiated or, for example, before surgery. The present inventions may also be used in combination with analgesic or other drugs used to elicit the wide variety of desired behavioral effects to increase the efficacy of the drugs or to decrease the required dosage.

Figure 7:
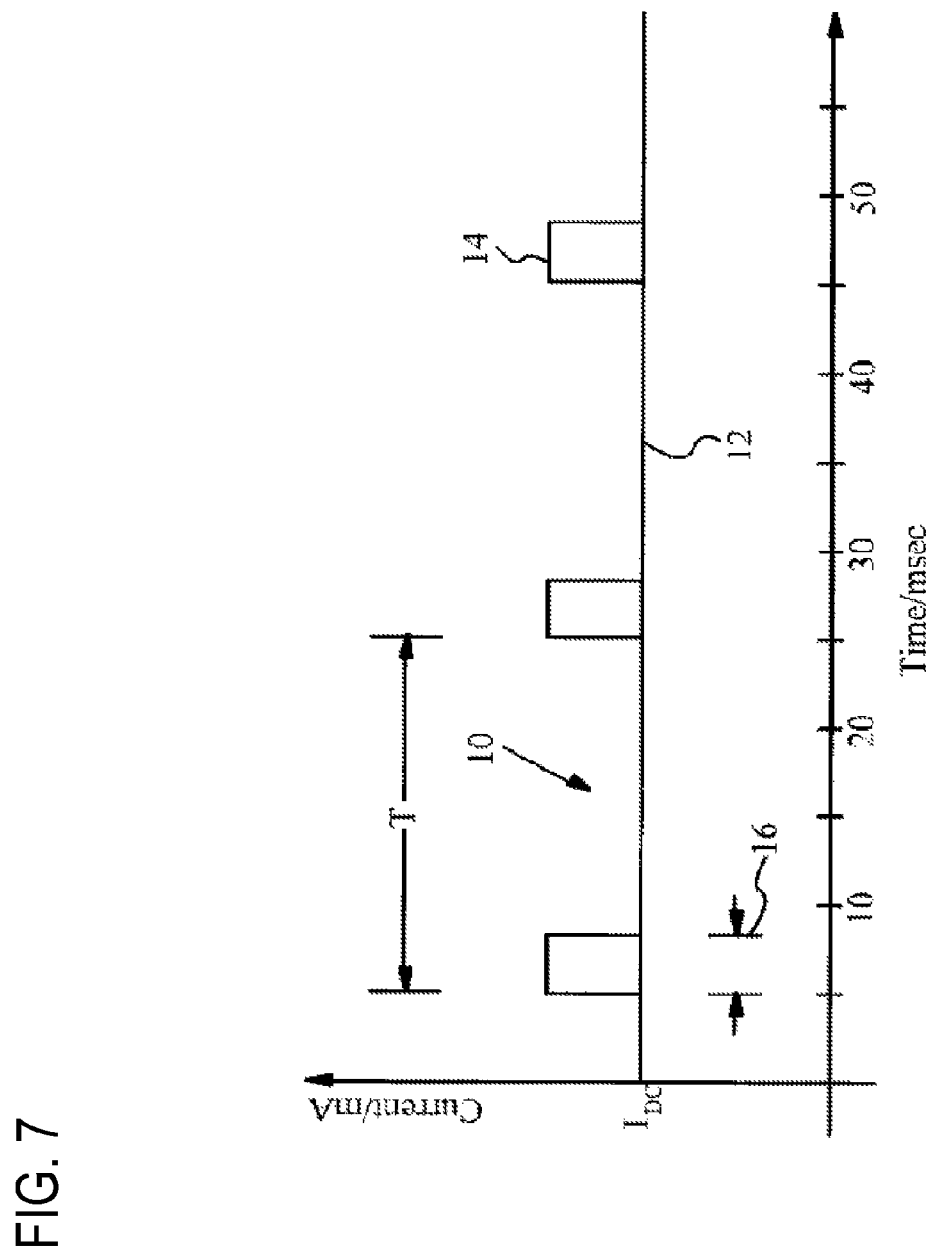
FIG. 7 is a diagram of a preferred unipolar AC pulse waveform for delivering TES according to the method of the present invention.

FIG. 7. Waveform 10 is a combination of direct current (DC) 12 and alternating current (AC) 14, which is in rectangular pulses. Rectangular current pulses begin at the current level of DC, $I_{DC}$. $I_{AC}$ is calculated as a Mean Absolute Deviation (MAD) value (also called an AC average) of the time-varying AC component; the peak-to-peak current value of pulses 14 is larger than $I_{AC}$. Preferably, the ratio of $I_{DC}$ to $I_{AC}$ is 2:1, but it may also be any value between 5:1 and 1:1. For example, if the ratio of $I_{DC}$ to $I_{AC}$ is 2:1 for a total current of 3 mA, $I_{DC}$ is 2 mA and $I_{AC}$ is 1 mA. It has been proposed that direct current reduces skin impedance, thereby allowing the AC current to penetrate the skin. The total current delivered is preferably between 0.2 and 20 mA, and most preferably between 2 and 10 mA. The pulse frequency is defined as 1/T, with T as shown in FIG. 7.

In some embodiments only AC current pulses are delivered to the subject, without being superimposed on DC current, for example to optimize the patient's response or to minimize the risk of superficial skin burns caused by DC current application. This embodiment may be preferred when the TES sessions are long and/or frequent.

In certain other embodiments, AC current is comprised of high frequency AC pulses of between about 1 kHz to about 10 MHz, modulated ("packed") into by low frequency AC current pulses, delivered at a low frequency 1-100 Hz, with preferred ranges of about 30(60)-100 Hz). In some cases a subject may respond better to DC current alone. This might occur for example when the TES electrodes are placed over the cutaneous areas overlaying the projections of the motor cortex, dorsolateral prefrontal cortex, occipital and somatosensory cortices, discussed below.

In another embodiment, the AC current pulses can be either unipolar or bipolar (bidirectional). Bipolar pulses enable the operator to deliver a zero net to the stimulated tissue under the TES electrodes to minimize the incidence and/or severity of local skin irritation and current-induced skin burns, and may also improve the efficacy of TES.

The bipolar AC current pulses can have different wave forms and durations, as long as the positive and negative wave surfaces of the pulse are equal in area to deliver the zero net charge.

Figure 8:
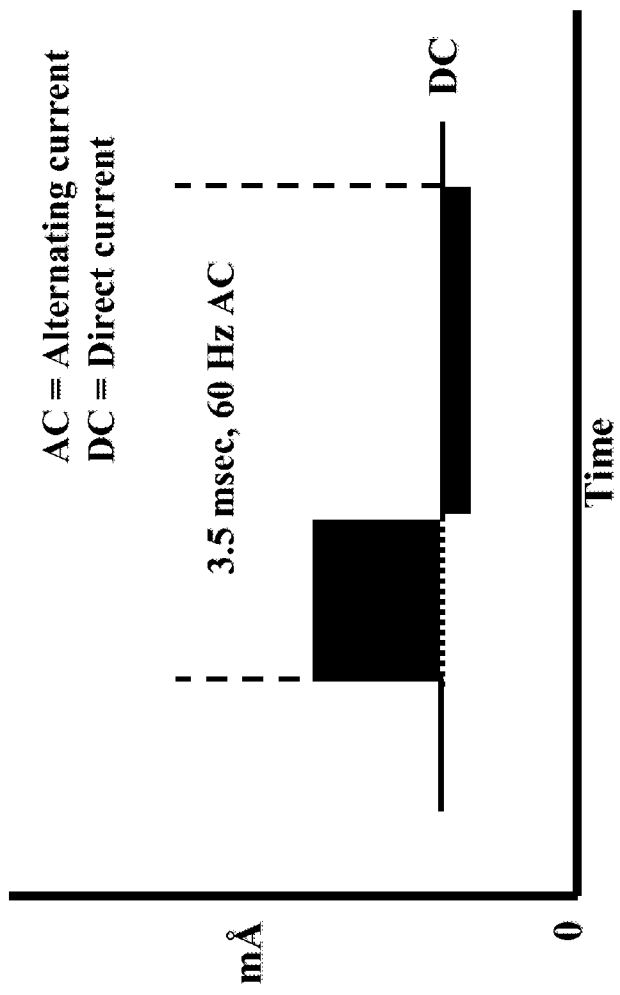
FIG. 8 Bipolar AC pulses, each of 3.5 msec duration, delivered at 60 Hz frequency. Note that the area of a positive "a" slope inside each pulse is equal to that of a negative "b" slope inside the pulse.
Figure 9:
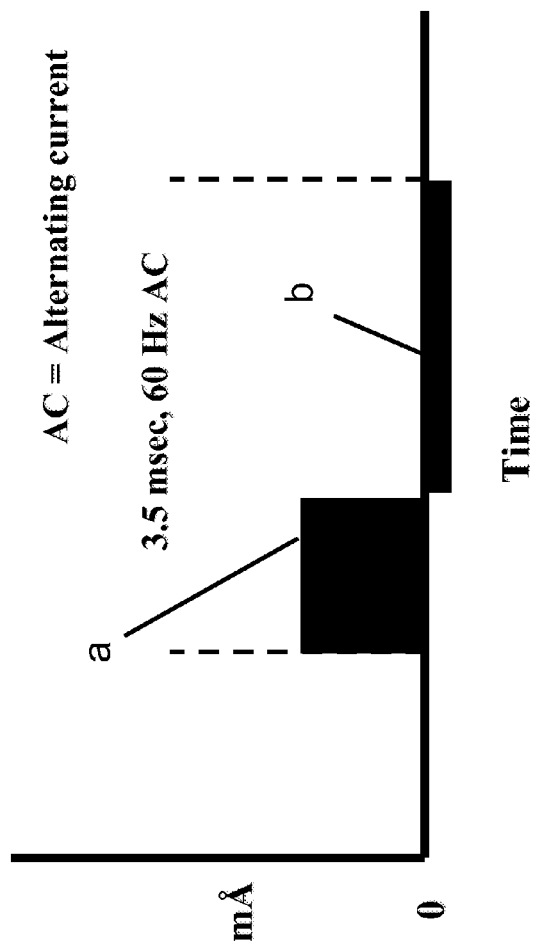
FIG. 9 Bipolar AC pulses, each of 3.5 msec duration, delivered at 60 Hz frequency. Note that the area of a positive "a" slope inside each pulse is equal to that of a negative "b" slope inside the pulse.
Figure 10:
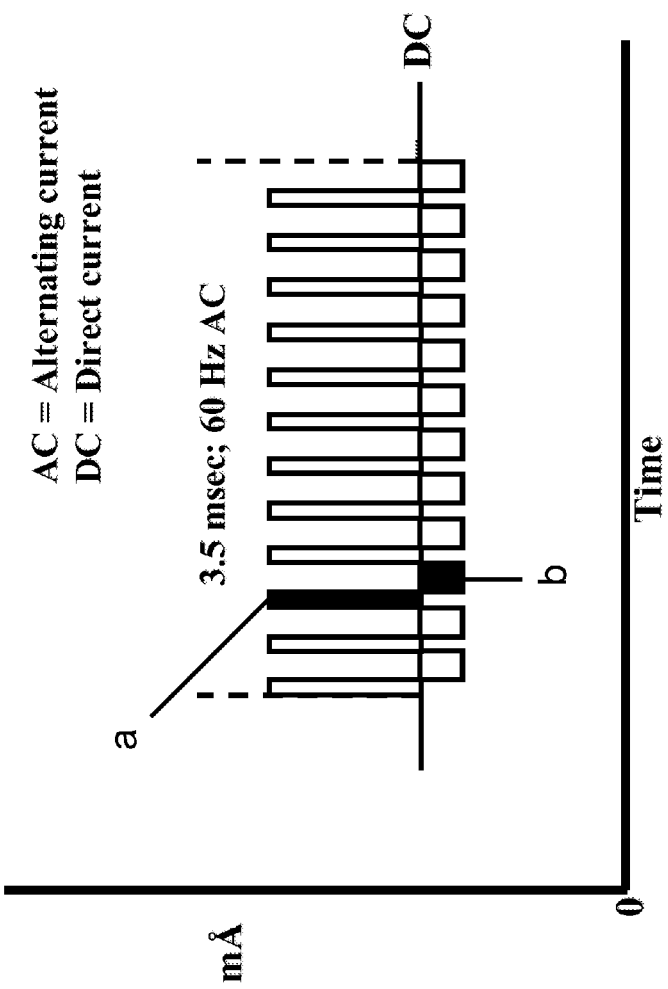
FIG. 10 High frequency bipolar AC pulses, modulated at 60 Hz frequency and delivered in "packs" 3.5 msec duration. Note that the area of a positive "a" slope of each pulse is equal to that of a negative "b" slope of the pulse.
Figure 11:
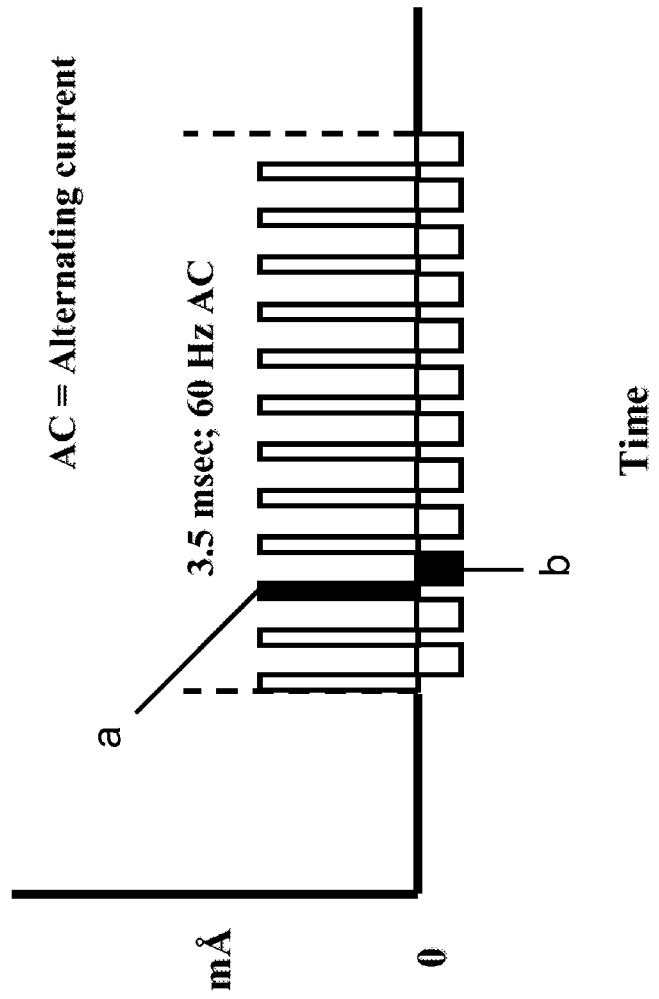
FIG. 11 High frequency bipolar AC pulses, modulated at 60 Hz frequency and delivered in "packs" 3.5 msec duration. Note that the area of a positive "a" slope of each pulse is equal to that of a negative "b" slope of the pulse.

FIG. 8 shows an example of bipolar (bidirectional) AC pulses that have a DC component. FIG. 9 shows an example of a bipolar (bidirectional) AC pulses without a DC component. FIG. 10 shows an example of bipolar (bidirectional) high frequency AC pulses, modulated by low frequency AC current pulses, with a DC component, and FIG. 11 shows an example of bipolar (bidirectional) high frequency AC pulses, modulated by low frequency AC current pulses, with a DC component.

Human Testing in the UVB Pain Model

The results of experiments described in Example 2 show that TES with DC:AC current, which has employed a precise skin electrode positioning described above, produced rapidly developing, frequency-dependent antihyperalgesic and systemic antialgesic effects in human subjects tested using the sunburn lesion (UVB ultraviolet burn) model, which is a validated model of inflammatory pain in humans that has been used to gauge the potency of different analgesic compounds. Experimental human models of pain and hyperalgesia are important tools for quantitative sensory testing (QST) and preclinical investigation of the efficacy of opioids and different analgesic compounds and treatments. UVB-induced hyperalgesia reproduces many components of peripheral inflammatory responses with sensitization of nociceptors (C and A delta fibers) and induction of primary hyperalgesic state, which follows tissue damage caused by injury, surgery or painful inflammatory disorders (e.g. arthritis).

20 healthy male subjects were tested to determine the anti-hyperalgesic and hypoalgesic effects of TES applied at two particular frequencies of DC:AC current: 60 Hz ($TES_{60\ Hz}$) and at 100 Hz ($TES_{100\ Hz}$) by evaluating to thermal heat and mechanical pain in experimentally induced ultraviolet B skin inflammation (UVB lesion) and normal skin. The study was conducted in a double-blind, randomized, two way crossover fashion. Electrodes were positioned as previously described. TES was administered for 35 min. at a constant frequency. Quantitative sensory testing (QST) evaluating heat and mechanical pain thresholds was conducted during TES and 45 min after TES was discontinued.

Administration of $TES_{60\ Hz}$ attenuated primary heat hyperalgesia in inflamed skin in a highly statistically significant manner (mean increase in HPTh: 1.2° C., 95% CI 0.7-1.6° C., $P<0.0001$), and also provided analgesic effect to noxious heat in intact skin (mean increase in HPTh: 0.3° C., 95% CI 0.0-0.6° C., $P<0.039$). In contrast, $TES_{100\ Hz}$ had no effect on HPTh in normal skin, and was 2.5 times less effective than $TES_{60\ Hz}$ in reducing primary heat hyperalgesia in a UVB lesion (mean increase in HPTh: 0.5° C., 95% CI 0.0-0.9° C., $P<0.037$). $TES_{60\ Hz}$ was highly effective in reducing primary mechanical hyperalgesia in a UVB lesion (mean increase in MPTh: 8.5 g, 95% CI 3.9-13.2 g, $P<0.0004$); there was also a trend towards statistically-significant analgesia to punctuate mechanical stimulation in normal skin (mean increase in MPTh: 5.8 g, 95% CI –1.0-12.5 g, $P<0.09$). $TES_{100\ Hz}$ had no effect on mechanical pain in an UVB lesion and normal skin. No post-stimulation hypoalgesia was observed with either TES modality. Administration of $TES_{100\ Hz}$ was associated with persistent presence of post-stimulation hyperalgesia to heat in normal skin 45 min after cessation of TES (mean decrease in HPTh: –0.4° C., 95% CI –0.1-0.7° C., $P<0.011$).

The results showed that the $TES_{60\ Hz}$ analgesic effect with AC:DC current in an inflamed (sunburn) lesion was either equivalent or slightly higher than administration of 800 mg of ibuprofen. The effect of TES vs. remifentanil was also tested. Remifentanil is a highly potent analgesic opioid, whose potency far exceeds that of intravenous morphine or alfentanyl, and is comparable to fentanyl, one of the most commonly used opioids intraoperatively and postoperatively. As expected remifentanil was significantly more effective (~2.5 times more potent) in attenuating thermal pain in normal human skin than was AC:DC stimulation with a constant frequency of 60 Hz ($TES_{60\ Hz}$). At a steady state concentration, a 0.05 $mcg \cdot kg^{-1} \cdot min^{-1}$ infusion of remifentanil increased HPTh in unimpaired skin in 50% of subjects by ~0.75° C. While remifentanil has a superior analgesic effect compared to $TES_{60\ Hz}$, the analgesic potency of $TES_{60\ Hz}$ to noxious heat in normal skin was 15 times higher than that observed after 0.08 $mcg \cdot kg^{-1}$ IV bolus of morphine. Importantly TES is nonaddictive.

These results support embodiments directed to treatment or prevention of chronic or acute pain syndrome using the TES stimulation methods herein described at particular frequencies ranging from about 10 Hz to about 100 Hz, preferably from about 30 Hz to about 65 Hz, and more preferably 60 Hz. Other medical conditions that can be similarly treated with the present TES methods at these frequencies include immune system depression, decreased wound healing, tissue and nerve regeneration, opiate and other drug withdrawal and neurological dysfunction.

Human Testing on Cognition and Mood

Human volunteer studies were performed in 20 subjects to access the effects of TES with DC:AC current at either 60 Hz ($TES_{60\ Hz}$) or at 100 Hz ($TES_{100\ Hz}$) on cognition and mood. The cognitive and mood tests used are described in Example 3. $TES_{60\ Hz}$ or $TES_{100\ Hz}$ were applied for approximately 35 minutes. The results on cognition showed that both frequencies increased concentration, the subjects' ability to perform tasks, and neurocognitive function, especially improving the quality of episodic secondary memory (Data not shown). Additional data on the mood modulating affect of TES, as assessed in POMS (Profile Of Mood States) scale, indicated a significant reduction on the subjects' Depression-Dejection score and a strong trend for reducing their Confusion-Bewilderment score, most notably associated with administration of 100 Hz TES. There were, however, no differences between the 60 Hz and 100 Hz TES groups in overall POMS scores. (Data not shown)

These results support embodiments for using TES as described herein to treat or prevent neurocognitive disorders, for example to improve learning, memory, or cognition, and mood disorders, as well as those states associated with sleep disturbances or deprivation. Medical conditions that can be treated with the TES methods of the present invention further include attention deficit disorder, anxiety, depression, mood disturbance, post-traumatic stress disorder, appetite disorders, Alzheimer's disease, Parkinson's disease and sexual dysfunction, treating normal fatigue, combat stress, and post traumatic stress syndrome. These conditions are treated using TES at frequencies from about 10 Hz to 100 Hz, more preferably from about 60 Hz to about 100 Hz. In addition to AC:DC current, AC or DC current alone can be used. The present TES methods can also be administered to normal subjects to improve learning or memory.

EXAMPLES

Example 1

TES Apparatus and Methodology

TES apparatus. The multipurpose TES device should be capable of providing a stable output current over a wide range of loads by utilizing an integrated circuit (IC) of the type XTR110 (Burr-Brown, Tucson, Ariz. USA) or similar, with simultaneous measurements by a digital panel voltmeter DMS-20PC (Datel, Inc., Mansfield, Mass. USA) or similar. The automatic computation of the AC MAD (Mean Absolute Deviation) value is performed by IC RMS (Root Means Square)-to-DC converter AD736 (Analog Devices, Norwood, Mass. USA) or similar. Stable frequency tuning over the desired range is provided by IC voltage-to-frequency converter AD654 (Analog Devices, Norwood, Mass. USA) or similar, which includes precision oscillator. The apparatus includes controls for manual adjustment of pulse duration, DC:AC ratio, TES frequency and the current value. Frequency and current values are continuously monitored on the front panel of the TES device.

Change in polarity of AC currents can be accomplished either manually or automatically approximately every 5-15 min.

Electric stimulators can be manufactured, with fixed and variable frequency and other parameter characteristics, both for in-hospital, ambulatory and home use. A device for home use is envisioned to be highly portable (e.g. purse or pocket size, clip-belt type, etc.), with autonomous and rechargeable power supply, but can also be stationary with the regular AC power supply.

Head gear holding the TES electrodes in place should be user-friendly and consist of a specially-designed cap or easily-assembled Velcro straps, or other applications, all of which should serve a specific purpose of holding the electrodes sufficiently tightly adhered to the specific skin areas of cutaneous stimulation of the skull, as described below.

TES Electrodes: Positioning and Size.

Proper electrode positioning over the specific anatomical landmarks related to the areas of cutaneous innervation of the skull by the GAN, GON, LON and supraorbital and supratrochlear nerves (FIG. 1) optimizes the analgesic and other neuromodulating effects of TES. Although the course of the GAN, GON and LON may be variable, FIGS. 3 and 4 demonstrate their relationship to the easily identifiable and reproducible anatomical landmarks of the head. The GON emerges from the nuchal muscles, on average, 1.5-4 cm lateral to external occipital protuberance (EOP) and 2 cm superior to intermastoid (IM) line (may also exit, on average, as low as 1 cm below the IM line), and branches approximately 0.5 cm superior to EOP. The LON emerges, on average, approximately 5-7 cm lateral to EOP, either at the IM line or above it, and frequently approximately at the midpoint between the EOP and IM lines or below the superior nuchal line. The GAN emerges, on average, 9 cm lateral to EOP and 1 cm above the mastoid tip.

The supraorbital nerve emerges from the orbit through the supraorbital foramen, which is easily palpable, and the supratrochlear nerve is medial to it (FIG. 1). Broad cutaneous distribution of the supraorbital nerve dictates that the electrodes should be positioned over relatively large skin area of the forehead. Once applied, each of the posterior electrodes overlaying the areas of cutaneous innervation by GON, LON and GAN shall be positioned in the manner to encompass the following approximate area, bordered by: outside—the mastoid process; inside—2 cm medial to the EOP; inferiorly—the IM line; superiorly—at least 1 cm above the EOP. The frontal electrode placed over the areas of cutaneous innervation by the supraorbital and supratrochlear nerves shall be positioned in the following manner: inferiorly, approximately at the level of the eyebrows, and extending superiorly, approximately to the hair line, along the lateral part of the orbit.

The sizes of the posterior and frontal electrodes can be configured individually for each patient to cover the described areas of cutaneous innervation, keeping in mind that the optimal size is at least about 5×5 cm for each of the posterior electrodes, and 5×10 cm for the frontal electrode. A larger electrode could decrease TES current density and the risk of skin burns during TES administration.

TES Electrodes: Composition and Configuration.

The removable TES electrodes typically incorporate in their structure electroconductive material(s) (EM) and an electrode interface (EI). TES electrodes can be composed of different materials, possess different degrees of rigidity and configuration, and manufactured through different fabrication methods and techniques that are well known in the art. EM relatively resistant to polarization, such as carbon, platinum, titanium, tantalum, gold or palladium-composed, containing or plated EM, or other types of materials or alloys with similar properties, are preferred. Stainless steel or other metals and/or EM are also acceptable, especially if enhanced with the EM resistant to polarization.

An EI can be achieved using liquid electrode interface (LEI), e.g. sponge, cloth (e.g. flannel, cotton, felt, etc.) or synthetic pads soaked in water or other electrically-conductive solution. For use with current invention, TES electrodes can be of various regular or irregular shapes, but the square and rectangular shapes may be preferred. Each of the LEI pads should be of sufficient thickness, having approximately 16 layers of cloth to allow administration of sufficient current while minimizing unpleasant sensations under the electrodes and risk of DC burns. The thickness can be varied. The LEI pads should be sufficiently wet to avoid an increase in skin resistance, however, excessive wetness should be avoided to prevent diversion of the current away from the targeted skin areas. An EI can also be achieved using other electrically-conductive substances (ECS), e.g. gel, paste, cream, etc. These can be used concomitantly or in lieu of LEI. Self-adhesive electrodes (SAE) of sufficient thickness and other characteristics counteracting the risk of DC skin burns (the so-called DC pads) can also be used either in lieu of EM, LEI and ECS, or in combination.

TES electrodes should be held in place during the procedure, for example with straps (e.g. Velcro straps) or specially designed headgear. Overly tight application of the electrodes should be avoided, and they should be held in place with minimal pressure sufficient to assure adequate contact with the skin. Where appropriate, EM and/or EI can be cut or adjusted, or reconfigured, to individually fit the areas of the individual patient's skull where TES electrodes are applied. To assure appropriate coverage of the areas of cutaneous innervation under the electrodes, both frontal and posterior TES electrodes can each be represented by a single or multiple electrodes.

TES: Technique of Administration.

In a preferred embodiment TES is administered over the single frontal and double (paired) posterior electrodes, as depicted in FIG. 1.

The frontal electrode is typically a cathode that is paired with the posterior electrodes that are anodes, however; the polarity can be changed during TES administration to reverse this relationship. Published tDC data suggests that it is possible to induce polarity-specific neuromodulating changes (increase or decrease in neuronal excitation). Such polarity-specific neuromodulating changes can be accomplished using the present improved TES methods by positioning the cathodal or anodal stimulation preferentially over the selected target area(s) or sites of cutaneous innervation to produce the polarity-specific effects.

The intensity of TES current is typically increased gradually depending on the individual patient's tolerance level to elicit a "strong, but comfortable" sensation under the electrodes, which typically indicates activation of Aδ fibers of primary cutaneous craniospinal afferent nerves. There should be no pain under the electrodes. The intensity of current can be adjusted up or down during TES administration, according to the patient's comfort level, but maintenance of a "strong, but comfortable" sensation for the larger period of time is strongly preferred.

Approximately 20 min of TES application should be sufficient to induce TES analgesic and/or other neuromodulating effects. This duration of stimulation can be adjusted, if deemed necessary or desired by the operator and/or patient. In an embodiment stimulation is for about 10-45 min, however significantly longer periods can be used. In some embodiments TES application is repeated multiple times during a single day with intervals adjusted according to patient tolerance and response, and to the condition being treated. Shorter TES duration minimizes the risk of DC skin burns, and therefore a change in stimulation polarity may not be necessary. However, the AC current pulse polarity can be changed to prevent adverse effects with longer periods of TES application, and/or if the patient notices "burning" or other unpleasant sensations under the electrodes during TES administration. TES can be applied over the course of weeks, months or years as needed.

In certain embodiments the frequency of stimulation ranges from about 30-65 Hz, for example to treat chronic or acute pain syndrome. In other embodiments a range of frequencies form about 60 to about 100 Hz is applied, for example to affect cognition or mood. The frequency and duration of stimulation vary depending not only on the patient but also on the condition being treated.

Example 2

Antihyperalgesic and Hypoalgesic Effects of TES in Validated Experimental Human Pain Models Methods. 20 healthy male subjects were tested to determine the antihyperalgesic and hypoalgesic effects of TES applied at 60 Hz ($TES_{60\ Hz}$) and at 100 Hz ($TES_{100\ Hz}$) by evaluating to thermal heat and mechanical pain in experimentally induced ultraviolet B skin inflammation (UVB lesion) and normal skin. The study was conducted in a double-blind, randomized, two way crossover fashion. TES was administered for 35 min. Quantitative sensory testing (QST) evaluating heat and mechanical pain thresholds was conducted during TES and 45 min after TES was discontinued.

A constant-current TES apparatus including controls for manual adjustment of pulse duration, DC:AC ratio, TES frequency and current value, that was in compliance with the safety standards established by the Hospital Instrumentation and Electrical Safety Committee of Stanford University was used. The TES current value was continuously displayed on the front panel of the TES device. Subjects were positioned in a recline chair, in a comfortable position. TES was administered through the frontal cathode (10×5 cm) positioned on the forehead above the eyebrows, and paired retromastoid anode (5×5 cm), all held in place by Velcro straps comfortably tightened over the subject's head. Positioning of the electrodes is important to optimize the results.

Each electrode had a stainless steel plate and a flannel pad soaked in water, and was brought in direct contact with the subject's skin. To standardize stimulation intensity for both TES modalities, current was gradually adjusted by the operator to achieve maximal tolerable, but comfortable (non-noxious) level, to a maximum of 5 mA, and maintained at that level for the entire duration of the TES procedure (the DC:AC current ratio was 2:1). In this example, the polarity is changed periodically, for example approximately every 10 minutes, but in other embodiments the polarity is not changed. In this embodiment the operator may change the polarity of stimulation manually for example approximately every 10 min, to prevent charge transfer caused by DC administration and reduce the risk of causing electrolytic skin burn. (I thought we also talked about the embodiment when we are NOT changing the polarity at all).

Statistical Analysis.

A power analysis indicated that studying 20 subjects would result in approximate 80% chance of obtaining statistical significance via repeated measures ANOVA, assuming a large effect size of 0.8. Treatment effects were analyzed with a linear mixed effects modeling approach using the lme function of S-Plus (version 6.2, Insightful, Seattle, Wash., USA). Mixed-effects models that account for correlation between repeated measures provide a more powerful and flexible tool for analyzing grouped data, compared to traditional statistics. Their use allows loosening of assumptions that may not be tenable, such as equal variances at different measurement points. Two levels of grouping were used: the factor subject and the factor date, indicating the day on which the experiment was conducted (random effects). The contrasts option was used to estimate the effect of the treatment levels ($TES_{60\ Hz}$ and $TES_{100\ Hz}$ during and after TES application) on HPTh and MPTH compared to the baseline value (fixed effects). $P<0.05$ was considered statistically significant.

FIG. 1 shows the positioning of the frontal (on left) and posterior (on right) TES electrodes over the projections of the peripheral craniospinal nerves. The TES electrodes overlie the retromastoid areas innervated by cutaneous branches of the greater occipital nerves (GON), lesser occipital nerves (LON) and greater auricular nerves (GAN), and the frontal area of the head innervated by cutaneous branches of the ophthalmic ($V_1$) division of the trigeminal nerve (supraorbital and supratrochlear nerves).

Results

A maximum intensity of AC:DC current (5 mA) was achieved for each study subject during each of the TES sessions, typically within first 5 min of stimulation, and it was maintained at that level throughout the entire TES procedure. The subjective tingling sensation under the TES electrodes during study sessions was identical for both TES modalities, assuring appropriate blinding of the subjects. The subjects tolerated the TES procedure well. One subject complained of a post-stimulation headache, which quickly subsided.

Figure 2:
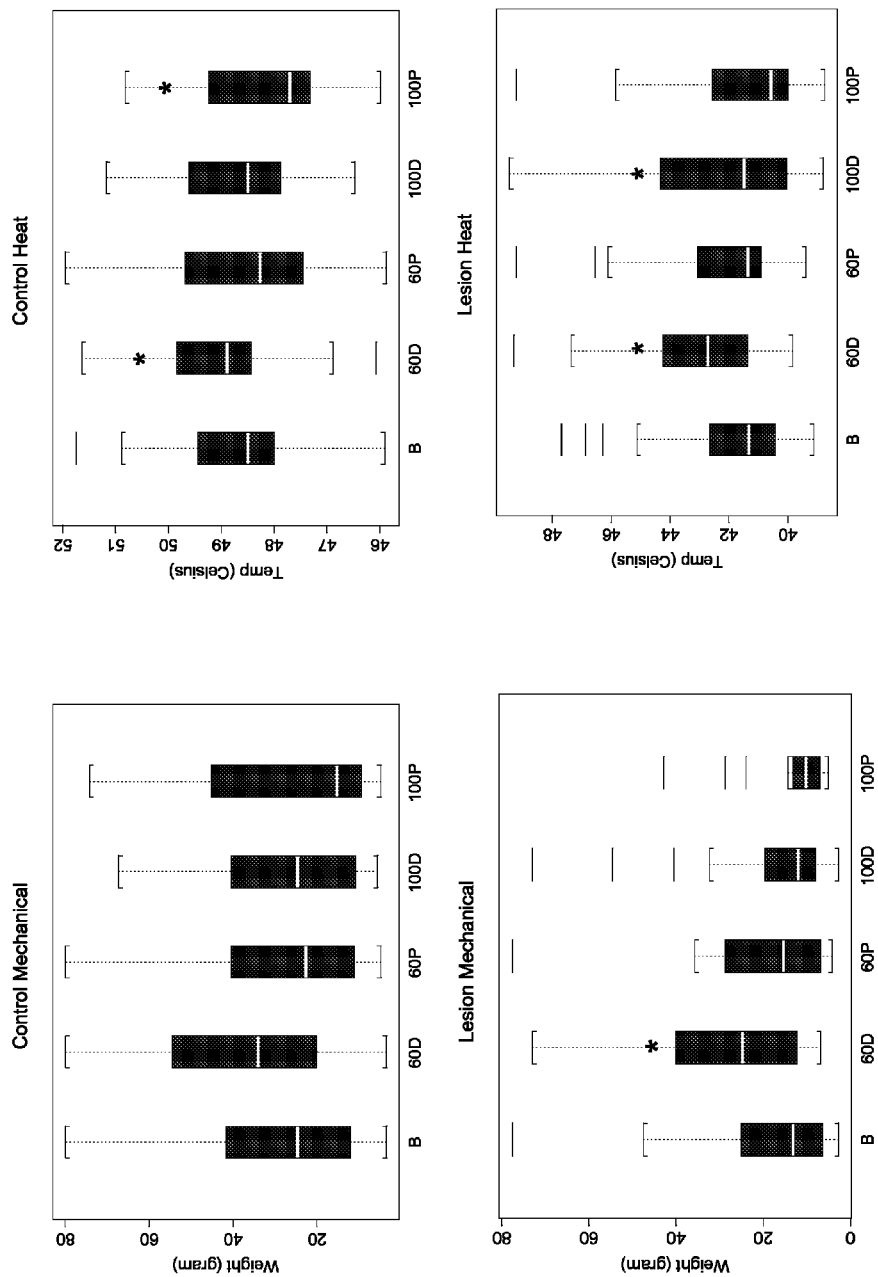
FIG. 2 shows the frequency-dependent analgesic effect of TES on nociceptive heat and mechanical pain thresholds (HPTh and MPTh) in normal skin and the sunburn (inflammatory, UVB) lesion in human volunteers. Control mechanical and Control heat—pain thresholds to nociceptive mechanical stimulation (gr) and heat (T°) in normal skin. Lesion mechanical and Lesion heat—pain thresholds to nociceptive mechanical stimulation (gr) and heat (T°) in the sunburn skin lesion (inflammatory pain). B—Baseline (pre-TES) values. 60 D and 100 D—Effect values during 60 Hz and 100 Hz TES. 60 P and 100 P—Effect values 45 min post 60 Hz and 100 Hz TES. Box plots show the distribution of the effects stratified by TES experimental group. The horizontal line in the interior of each box is the median. The height of the box is the interquartile distance, which is the difference between the third quartile and first quartile. The whiskers extend to a distance of 1.5 times the interquartile distance. Horizontal lines indicate outliers. An asterisk indicates a median value statistically different from baseline ($P<0.05$).

FIG. 2 shows the effect of different TES frequencies on heat and mechanical pain thresholds (HPTh and MPTh) in normal skin and with ultra violet burn (UVB) lesion, stratified by TES treatment group and time. Box plots show the change in HPTh and MPTh stratified by TES treatment group and time. The horizontal line in the interior of each box is the median. The height of the box is the interquartile distance, which is the difference between the third quartile and first quartile. The whiskers extend to a distance of 1.5 times the interquartile distance. Horizontal lines indicate outliers. An asterisk indicates a median value statistically different from the baseline (*$P<0.05$). B: baseline; 60 D and 100 D: HPTh and MPTh during $TES_{60\ Hz}$ and $TES_{100\ Hz}$; 60 P and 100 P: HPTh and MPTh post $TES_{60\ Hz}$ and $TES_{100\ Hz}$.

Tables A-D provide model estimates of the real population values, which were well fitted with the measured means. The development of primary thermal and mechanical hyperalgesia was confirmed in UVB lesion, as evidenced by decreased HPTh and MPTh at the site of inflammation (HPTh mean decrease 6.8° C., 95% CI 6.2-7.3° C.; MPTh mean decrease 11.6 g, 95% CI 9.5-13.6 g.

Example 3

A. Cognitive Drug Research System Battery of Tests

Figure 6:
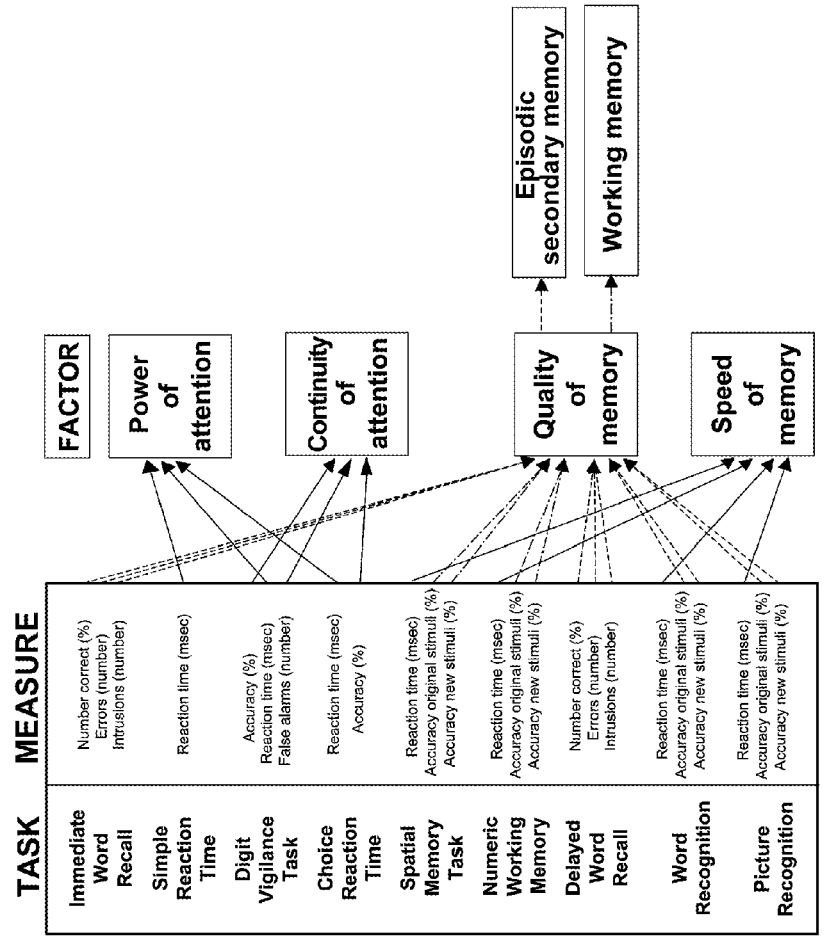
FIG. 6 Schematic representation of the CDR battery of tests.

Human volunteer studies were performed using TES stimulation at two frequencies: about 60 Hz and about 100 Hz for approximately 35 minutes. The results showed increased concentration and ability to perform tasks, and increased neurocognitive function, especially improving the quality of episodic secondary memory at both frequencies. Assessment of the subjects' cognitive function was conducted using an FDA-approved, computerized Cognitive Drug Research System battery of tests (herein "CDR tests") (United BioSource Corporation, Bethesda, Md. USA), administered at baseline (15 min prior to each TES session), and again 15 min after the end of each TES session. The CDR tests have been used extensively in clinical trials for over 20 years; it demonstrates good test-retest reliability, excellent criterion validity, discriminant validity and construct validity. They are sensitive to a variety of pharmacological and non-pharmacological modulation of cognitive function, in both healthy individuals and multiple disease states. Parallel forms of the CDR tests are presented to a subject at each testing session on a high resolution computer monitor in easy to read fonts, always in the same order. The subject's responses (with the exception of written word recall tests, which are scored manually), are automatically recorded on encrypted files when the subject pushes (YES/NO) response buttons. The CDR tests assess cognitive function in five major domains (factors): Power of Attention, Continuity of Attention, Quality of Episodic Secondary Memory, Quality of Working memory, and Speed of Memory. FIG. 6. The three attention tasks (simple reaction time, choice reaction time, digit vigilance) and five memory tasks (immediate word recall, spatial memory, numeric working memory, delayed word recall, word recognition, picture recognition) are collapsed into five composite outcome factors derived by factor analysis. There are two composite outcome factors for attention (Power of Attention and Continuity of Attention), and three for memory (Quality of Episodic Secondary Memory, Quality of Working Memory, and Speed of Memory). Arrows indicate a single task outcome measure contribution to the given factor. Dotted lines indicate contribution of a single task outcome measure to both Quality of Memory (either Episodic Secondary Memory or Working Memory) and Speed of Memory. Wesnes K., Memory, Basic Concepts, Disorders and Treatment. Edited by Peter Paul De Deyn, et al. Uitgeverij Acco, Leuven, 2003, pp. 453-72; Roth T., et al, Sleep Breath 2008; 12:53-62; Fleming K., et al., Biol Psychiatry 1997; 41(1):43-9; Silver H, et al., Am J Psychiatry 2003; 160(10):1809-16.

B. Composite Cognitive Outcome Factors

The Power of Attention is derived by combining the speeds of a simple reaction time, choice reaction time, and digit vigilance tasks, and reflects the intensity (speed) of concentration. It reflects an ability to focus concentration on a particular topic for a relatively short period of time. The Continuity of Attention is derived by combining the accuracy of correct decisions in choice reaction time and digit vigilance tasks, with correct detection of false alarms. It shows an ability to sustain concentration (vigilance) for a prolonged period of time. The Quality of Episodic Secondary Memory is derived by combining the accuracy of recalling the words in the immediate and delayed word recall tasks (the recalled words are written down by the subject), with correct recognition of the previously and newly presented words and pictures on the computer monitor. It reflects an ability to store, hold and retrieve information of an episodic nature from the long-term memory. The Quality of Working Memory is obtained by combining the sensitivity scores from the two working memory tests—numeric and spatial working memory. It reflects an ability for short-term retention or processing of verbal and visuospatial information in two subsystems of short-term working memory—the phonological loop and the visuospatial scratch pad, respectively. The integrity of these subsystems is essential to the capacity to maintain in working memory the representations that may form a substrate for mental operations. The Speed of Memory is derived by combining the reaction times of working memory tasks (spatial working memory and numeric working memory) with episodic recognition tasks (delayed word recognition and delayed picture recognition). It reflects the time required to correctly decide whether an item is held in working memory or episodic secondary memory.

C. Subjective Mood Measures

The Bond and Lader Visual Analogue Scales (VAS), consisting of 16 VAS anchored by antonyms (e.g. alert-drowsy, lethargic-energetic, etc.), were combined to form three mood factors: alertness, calmness and contentment. See References for CDR Testing. Mood assessment was also conducted in the pencil-and-paper Profile of Mood States (POMS) test, which reliably assesses affective mood state fluctuations in response to therapeutic interventions in a wide variety of populations. The standard POMS utilizes a 65-item, 5-point adjective rating scale, assessing such mood factors as tension anxiety, depression-dejection, anger-hostility, vigor-activity, fatigue-inertia and confusion-bewilderment. Similar to the CDR battery of tests, POMS was administered at baseline (15 min prior to each TES session), and 15 min after each TES session was discontinued. Comprehensive self-assessment diaries were also designed, to evaluate possible long-lasting effects of TES on mood and emotional state, alertness and sleep. They were filled out by the subjects daily throughout the study period, and returned to the study investigators via e-mail. The diaries were largely based on the Positive Affect Negative Affect Scale (PANAS). The PANAS is a 20-item, 5-point adjective rating scale of feelings and emotions, yielding reliable scores for assessing such self-rated dominant dimensions of emotional experience as positive affect (PA) and negative affect (NA). McNair D M, Lorr M, Droppleman L F. Edits Manual for the Profile of Mood States. Revised. 1992. Edits/Educational and Industrial Testing Service, San Diego, Calif. Watson D, Clark L A, Tellegen A. Development and validation of brief measures of positive and negative affect: the PANAS scales. J Pers Soc Psychol 1988; 54:1063-70.

In the foregoing specification, the invention has been described with reference to specific embodiments. It will, however, be evident that various modifications and changes may be made without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

REFERENCES

1. Limoge A, Robert C, Stanley T H. Transcutaneous cranial electrical stimulation (TCES): a review 1998. Neurosci Biobehav Rev 1999; 23:529-38.
2. Lebedev V P, Malygin A V, Kovalevski A V, et al. Devices for noninvasive transcranial electrostimulation of the brain endorphinergic system: application for improvement of human psycho-physiological status. Artif Organs 2002; 26:248-51.
3. Klawansky S, Yeung A, Berkey C, et al. Meta-analysis of randomized controlled trials of cranial electrostimulation efficacy in treating selected psychological and physiological conditions. J Nerv Ment Dis 1995; 183:478-84.
4. Stinus L, Auriacombe M, Tignol J, et al. Transcranial electrical stimulation with high frequency intermittent current (Limoge's) potentiates opiate-induced analgesia: blind studies. Pain 1990; 42:351-63.
5. Mantz J, Azerad J, Limoge A, Desmonts J M. Transcranial electrical stimulation with Limoge's currents decreases halothane requirements in rats: evidence for the involvement of endogenous opioids. Anesthesiology 1992; 76:253-60.
6. Nekhendzy V, Fender C P, Davies M F, et al. The antinociceptive effect of transcranial electrostimulation with combined direct and alternating current in freely moving rats. Anesth Analg 2004; 98:730-7.
7. Dewey W L, Harris L S. The tail-flick test. In: Ehrenpreis S, Neidle A, eds. Methods in narcotic research. New York: Marcel Dekker, 1975: 101-9.
8. Vladimirov M, Nau C, Mok W M, Strichartz G. Potency of bupivacaine stereoisomers tested in vitro and in vivo: biochemical, electrophysiological, and neurobehavioral studies. Anesthesiology 2000; 93:744-55.
9. Kalra A, Urban M O, Sluka K A. Blockade of opioid receptors in rostral ventral medulla prevents antihyperalgesia produced by transcutaneous electrical nerve stimulation (TENS). J Pharmacol Exp Ther 2001; 298:257-63.
10. Woolf C J, Mitchell D, Barrett G D. Antinociceptive effect of peripheral segmental electrical stimulation in the rat. Pain 1980; 8:237-52.
11. Yeomans J S. Principles of brain stimulation. New York: Oxford University Press, 1990.
12. Kano T, Cowan G S, Smith R H. The role of the somatosensory system in general electroanesthesia. Anesth Analg 1974; 53:667-71.
13. Tatsuno J, Zouhar R J, Smith R H, Cullen S C. Electroanesthesia studies: the target area for electroanesthesia. Anesth Analg 1967; 46(4):432-9.
14. Kano T, Cowan G S, Smith R H. Electroanesthesia (EA) studies: EA produced by stimulation of sensory nerves of the scalp in rhesus monkeys. Anesth Analg 1976; 55:536-41.
15. Becser N, Bovim G, Sjaastad O. Extracranial nerves in the posterior part of the head: anatomic variations and their possible clinical significance. Spine 1998; 23:1435-41.
16. Pinosky M L, Fishman R L, Reeves S T, et al. The effect of bupivacaine skull block on the hemodynamic response to craniotomy. Anesth Analg 1996; 83:1256-61.
17. Greene E C. Anatomy of the rat. New York: Hafner, 1959, c1935.
18. Scheurer S, Gottschall J, Groh V. Afferent projections of the rat major occipital nerve studied by transganglionic transport of HRP. Anat Embryol 1983; 167:425-38.
19. Liu D, Hu Y. The central projections of the great auricular nerve primary afferent fibers—an HRP transganglionic tracing method. Brain Res. 1988; 445:205-10.
20. Bartsch T, Goadsby P J. Stimulation of the greater occipital nerve induces increased central excitability of dural afferent input. Brain 2002; 125:1496-509.
21. Ranson S W, Droegemueller W H, Davenport H K, Fisher C. Number size and myelination of the sensory fibers in the cerebrospinal nerves. (Chapter 1: Sensation: Its mechanisms and disturbance) Proc Assn Res Nerv Ment Dis 1934; 3-34.
22. Pfaller K, Arvidsson J. Central distribution of trigeminal and upper cervical primary afferents in the rat studied by anterograde transport of horseradish peroxidase conjugated to wheat germ agglutinin. J Comp Neurol. 1988; 268:91-108.
23. Imamura J, Saunders M C, Keller J T. Projections of cervical nerves to the rat medulla. Neurosci Lett. 1986; 70:46-51.
24. Fitz-Ritson D. The direct connections of the C2 dorsal root ganglia in the *Macaca irus* monkey: relevance to the chiropractic profession. J Manipulative Physiol Ther 1985; 8:147-56.
25. Neuhuber W L, Zenker W. Central distribution of cervical primary afferents in the rat, with emphasis on proprioceptive projections to vestibular, perihypoglossal, and upper thoracic spinal nuclei. J Comp Neurol 1989; 280:231-53.
26. Abrahams V C, Richmond F J, Keane J. Projections from C2 and C3 nerves supplying muscles and skin of the cat neck: a study using transganglionic transport of horseradish peroxidase. J Comp Neurol 1984; 230:142-54.
27. Bartsch T, Goadsby P J. Increased responses in trigeminocervical nociceptive neurons to cervical input after stimulation of the dura mater. Brain 2003; 126:1801-13.
28. Marfurt C F. The central projections of trigeminal primary afferent neurons in the cat as determined by the tranganglionic transport of horseradish peroxidase. J Comp Neurol 1981; 203:785-98.
29. Phelan K D, Falls W M. The spinotrigeminal pathway and its spatial relationship to the origin of trigeminospinal projections in the rat. Neuroscience 1991; 40:477-96.
30. Marfurt C F, Rajchert D M. Trigeminal primary afferent projections to "non-trigeminal" areas of the rat central nervous system. J Comp Neurol 1991; 303:489-511.
31. Beckstead R M, Norgren R. An autoradiographic examination of the central distribution of the trigeminal, facial, glossopharyhgeal, and vagal nerves in the monkey. J Comp Neurol 1979; 184:455-72.
32. Dado R J, Katter J T, Giesler G J Jr. Spinothalamic and spinohypothalamic tract neurons in the cervical enlargement of rats. III. Locations of antidromically identified axons in the cervical cord white matter. J Neurophysiol 1994; 71:1003-21.
33. Boivie J. Thalamic projections from lateral cervical nucleus in monkey. A degeneration study. Brain Res 1980; 198:13-26.
34. Keay K A, Feil K, Gordon B D, Herbert H, Bandler R. Spinal afferents to functionally distinct periaqueductal gray columns in the rat: an anterograde and retrograde tracing study. J Comp Neurol 1997; 385:207-29.
35. Krout K E, Jansen A S, Loewy A D. Periaqueductal gray matter projection to the parabrachial nucleus in rat. J Comp Neurol 1998; 401:437-54.
36. Benarroch E E. Pain-autonomic interactions: a selective review. Clin Auton Res 2001; 11:343-9.
37. Lue J H, Leong S M, Day A S, et al. Changes in c-Fos protein expression in the rat cuneate nucleus after electric stimulation of the transected median nerve. J Neurotrauma 2002; 19:897-907.
38. Day A S, Lue J H, Sun W Z, et al. A beta-fiber intensity stimulation of chronically constricted median nerve induces c-fos expression in thalamic projection neurons of the cuneate nucleus in rats with behavioral signs of neuropathic pain. Brain Res 2001; 895:194-203.
39. Urasaki E, Wada S, Yasukouchi H, Yokota A. Effect of transcutaneous electrical nerve stimulation (TENS) on central nervous system amplification of somatosensory input. J Neurol 1998; 245:143-8.

40. Harmann P A, Carlton S M, Willis W D. Collaterals of spinothalamic tract cells to the periaqueductal gray: a fluorescent double-labeling study in the rat. Brain Res 1988; 441:87-97.
41. Cliffer K D, Burstein R, Giesler G J Jr. Distributions of spinothalamic, spinohypothalamic, and spinotelencephalic fibers revealed by anterograde transport of PHA-L in rats. J Neurosci 1991; 11:852-68.
42. Dado R J, Katter J T, Giesler G J Jr. Spinothalamic and spinohypothalamic tract neurons in the cervical enlargement of rats. I. Locations of antidromically identified axons in the thalamus and hypothalamus. J Neurophysiol 1994; 71:959-80.
43. Dado R J, Katter J T, Giesler G J Jr. Spinothalamic and spinohypothalamic tract neurons in the cervical enlargement of rats. II. Responses to innocuous and noxious mechanical and thermal stimuli. J Neurophysiol 1994; 71:981-1002.
44. Yezierski R P, Mendez C M. Spinal distribution and collateral projections of rat spinomesencephalic tract cells. Neuroscience 1991; 44:113-30.
45. Menetrey D, Basbaum A I. Spinal and trigeminal projections to the nucleus of the solitary tract: a possible substrate for somatovisceral and viscerovisceral reflex activation. J Comp Neurol 1987; 255:439-50.
46. Gamboa-Esteves F O, Tavares I, Almeida A, et al. Projection sites of superficial and deep spinal dorsal horn cells in the nucleus tractus solitarii of the rat. Brain Res 2001; 921:195-205.
47. Burstein R, Cliffer K D, Giesler G J Jr. Cells of origin of the spinohypothalamic tract in the rat. J Comp Neurol 1990; 291:329-44.
48. Burstein R, Giesler G J Jr. Retrograde labeling of neurons in spinal cord that project directly to nucleus accumbens or the septal nuclei in the rat. Brain Res 1989; 497:149-54.
49. Burstein R, Dado R J, Giesler G J Jr. The cells of origin of the spinothalamic tract of the rat: a quantitative reexamination. Brain Res 1990; 511:329-37.
50. Newman H M, Stevens R T, Apkarian A V. Direct spinal projections to limbic and striatal areas: anterograde transport studies from the upper cervical spinal cord and the cervical enlargement in squirrel monkey and rat. J Comp Neurol 1996; 365:640-58.
51. Kemplay S K, Webster K E. A qualitative and quantitative analysis of the distributions of cells in the spinal cord and spinomedullary junction projecting to the thalamus of the rat. Neuroscience 1986; 17:769-89.
52. Dougherty P M, Schwartz A, Lenz F A. Responses of primate spinomesencephalic tract cells to intradermal capsaicin. Neuroscience 1999; 90:1377-92.
53. Boscan P, Paton J F. Excitatory convergence of periaqueductal gray and somatic afferents in the solitary tract nucleus: role for neurokinin 1 receptors. Am J Physiol Regul Integr Comp Physiol 2005; 288:R262-9.
54. Feil K, Herbert H. Topographic organization of spinal and trigeminal somatosensory pathways to the rat parabrachial and Kolliker-Fuse nuclei. J Comp Neurol 1995; 353:506-28.
55. Kitamura T, Yamada J, Sato H, Yamashita K. Cells of origin of the spinoparabrachial fibers in the rat: a study with fast blue and WGA-HRP. J Comp Neurol 1993; 328:449-61.
56. Bernard J F, Dallel R, Raboisson P, et al. Organization of the efferent projections from the spinal cervical enlargement to the parabrachial area and periaqueductal gray: a PHA-L study in the rat. J Comp Neurol 1995; 353:480-505.
57. Malick A, Strassman R M, Burstein R. Trigeminohypothalamic and reticulohypothalamic tract neurons in the upper cervical spinal cord and caudal medulla of the rat. J Neurophysiol 2000; 84:2078-112.
58. Burstein R, Cliffer K D, Giesler G J Jr. Direct somatosensory projections from the spinal cord to the hypothalamus and telencephalon. J Neurosci 1987; 7:4159-64.
59. Kostarczyk E, Zhang X, Giesler G J Jr. Spinohypothalamic tract neurons in the cervical enlargement of rats: locations of antidromically identified ascending axons and their collateral branches in the contralateral brain. J Neurophysiol 1997; 77:435-51.
60. Villanueva L, de Pommery J, Menetrey D, Le Bars D. Spinal afferent projections to subnucleus reticularis dorsalis in the rat. Neurosci Lett 1991; 134:98-102.
61. Villanueva L, Bouhassira D, Le Bars D. The medullary subnucleus reticularis dorsalis (SRD) as a key link in both the transmission and modulation of pain signals. Pain 1996; 67:231-40.
62. Le Bars D. The whole body receptive field of dorsal horn multireceptive neurones. Brain Res Rev 2002; 40:29-44.
63. Granum S L. The spinothalamic system of the rat. I. Locations of cells of origin. J Comp Neurol 1986; 247:159-80.
64. Chudler E H, Foote W E, Poletti C E. Responses of cat C1 spinal cord dorsal and ventral horn neurons to noxious and non-noxious stimulation of the head and face. Brain Res 1991; 555:181-92.
65. Sessle B J, Hu J W, Amano N, Zhong G. Convergence of cutaneous, tooth pulp, visceral, neck and muscle afferents onto nociceptive and non-nociceptive neurones in trigeminal subnucleus caudalis (medullary dorsal horn) and its implications for referred pain. Pain 1986; 27:219-35.
66. Slugg R M, Light A R. Spinal cord and trigeminal projections to the pontine parabrachial region in the rat as demonstrated with Phaseolus vulgaris leucoagglutinin. J Comp Neurol 1994; 339:49-61.
67. Goadsby P J, Hoskin K L. The distribution of trigeminovascular afferents in the nonhuman primate brain *Macaca nemestrina*: a c-fos immunocytochemical study. J Anat 1997; 190:367-75.
68. Hoskin K L, Bulmer D C, Lasalandra M, et al. Fos expression in the midbrain periaqueductal grey after trigeminovascular stimulation. J Anat 2001; 198:29-35.
69. Goadsby P J, Knight Y E, Hoskin K L. Stimulation of the greater occipital nerve increases metabolic activity in the trigeminal nucleus caudalis and cervical dorsal horn of the cat. Pain 1997; 73:23-8.
70. Piovesan E J, Kowacs P A, Tatsui C E, et al. Referred pain after painful stimulation of the greater occipital nerve in humans: evidence of convergence of cervical afferences on trigeminal nuclei. Cephalalgia 2001; 21:107-9.
71. Boscan P, Pickering A E, Paton J F. The nucleus of the solitary tract: an integrating station for nociceptive and cardiorespiratory afferents. Exp Physiol 2002; 87:259-66.
72. DaSilva A F, Becerra L, Makris N, et al. Somatotopic activation in the human trigeminal pain pathway. J Neurosci 2002; 22:8183-92.
73. Gabis L, Shklar B, Geva D. Immediate influence of transcranial electrostimulation on pain and beta-endorphin blood levels: an active placebo-controlled study. Am J Phys Med Rehabil 2003; 82:81-5.
74. Capel I D, Dorrell H M, Spencer E P, Davis M W. The amelioration of the suffering associated with spinal cord injury with subperception transcranial electrical stimulation. Spinal Cord 2003; 41:109-17.

75. Joy M L G, Lebedev V P, Gati J S. Imaging of current density and current pathways in rabbit brain during Transcranial electrostimulation. IEEE Trans Biomed Eng 1999; 46:1139-49.

76. Almay B G, Johansson F, von Knorring L, et al. Long-term high frequency transcutaneous electrical nerve stimulation (hi-TNS) in chronic pain. Clinical response and effects on CSF-endorphins, monoamine metabolites, substance P-like immunoreactivity (SPLI) and pain measures. J Psychosom Res; 29:247-57.

77. Salar G, Job I, Mingrino S, et al. Effect of transcutaneous electrotherapy on CSF beta-endorphin content in patients without pain problems. Pain 1981; 10:169-72.

78. Liss S, Liss B. Physiological and therapeutic effects of high frequency electrical pulses. Integr Physiol Behav Sci 1996; 31:88-95.

79. Han J S, Chen X H, Sun S L, et al. Effect of low- and high-frequency TENS on Met-enkephalin-Arg-Phe and dynorphin A immunoreactivity in human lumbar CSF. Pain 1991; 47:295-8.

80. Liu X, Zhu B, Zhang S X. Relationship between electroacupuncture analgesia and descending pain inhibitory mechanism of nucleus raphe magnus. Pain 1986; 24:383-96.

81. Warner R L, Johnston C, Hamilton R, et al. Transcranial electrostimulation effects on rat opioid and neurotransmitter levels. Life Sci 1994; 54:481-90.

82. Sjölund B H. Peripheral nerve stimulation suppression of C-fiber-evoked flexion reflex in rats. J Neurosurg 1985; 63:612-6.

83. Chung J M, Lee K H, Hori Y, et al. Factors influencing peripheral nerve stimulation produced inhibition of primate spinothalamic tract cells. Pain 1984; 19:277-93.

84. Chan C W, Tsang H Inhibition of the human flexion reflex by low intensity, high frequency transcutaneous electrical nerve stimulation (TENS) has a gradual onset and offset. Pain 1987; 28:239-53.

85. Lee K H, Chung J M, Willis W D. Inhibition of primate spinothalamic tract cells by TENS. J Neorosurg 1985; 62:276-87.

86. Hu J W. Response properties of nociceptive and non-nociceptive neurons in the rat's trigeminal subnucleus caudalis (medullary dorsal horn) related to cutaneous and deep craniofacial afferent stimulation and modulation by diffuse noxious inhibitory controls. Pain 1990; 41:331-45.

87. Bouhassira D, Bing Z, Le Bars D. Studies of brain structures involved in diffuse noxious inhibitory controls in the rat: the rostral ventromedial medulla. J Physiol 1993; 463: 667-87.

88. Sandkuhler J. The organization and function of endogenous antinociceptive systems. Prog Neurobiol 1996; 50:49-81.

89. Limoge A: An introduction to electroanesthesia. Baltimore. University Park Press, 1975, pp 9-10, 15-21, 44-8

90. Kirsch D L, Smith R B: The use of cranial electrotherapy stimulation in the management of chronic pain: A review. NeuroRehabilitation 2000; 14(2): 85-94.

91. Williams J A, Imamura M, and Fregni F: Updates on the use of non-invasive brain stimulation in physical and rehabilitation medicine. J Rehabil Med 2009; 41(5): 305-11.

92. Zanardi R, Barbini B, Rossini D, Bernasconi A, Fregni F, Padberg F, Rossi S, Wirz-Justice A, Terman M, Martiny K, Bersani G, Hariri A R, Pezawas L, Roiser J P, Bertolino A, Calabrese G, Magri L, Benedetti F, Pontiggia A, Malaguti A, Smeraldi E, and Colombo C: New perspectives on techniques for the clinical psychiatrist: Brain stimulation, chronobiology and psychiatric brain imaging. Psychiatry Clin Neurosci 2008; 62(6): 627-37.

93. Albert G C, Cook C M, Prato F S, and Thomas A W: Deep brain stimulation, vagal nerve stimulation and transcranial stimulation: An overview of stimulation parameters and neurotransmitter release. Neurosci Biobehav Rev 2009 May 9. [Epub ahead of print].

94. Nekhendzy V, Fender C P, Davies M F, Lemmens H J, Kim M S, Bouley D M, and Maze M: The antinociceptive effect of transcranial electrostimulation with combined direct and alternating current in freely moving rats. Anesth Analg 2004; 98(3): 730-7.

95. Nekhendzy V, Davies M F, Lemmens H J, and Maze M: The role of the craniospinal nerves in mediating the antinociceptive effect of transcranial electrostimulation in the rat. Anesth Analg 2006; 102(6): 1775-80.

96. Anan'ev G, Golubeva I V, Gurova E V, Kaschevskaia L A, Levitsaia A, and Khudyi Y B: Preliminary data on experimental electronarcosis induced with apparatus of the Scientific Research Institute of Experimental Surgical Apparatus and Instruments. Anesthesiology 1960; 21: 215-9

97. Mignon A, Laudenbach V, Guischard F, Limoge A, Desmonts J M, and Mantz J: Transcutaneous cranial electrical stimulation (Limoge's currents) decreases early buprenorphine analgesic requirements after abdominal surgery. Anesth Analg 1996; 83(4): 771-5.

98. Gabis L, Shklar B, and Geva D: Immediate influence of transcranial electrostimulation on pain and beta-endorphin blood levels: an active placebo-controlled study. Am J Phys Med Rehabil 2003; 82: 81-5

99. Akoev G N, Il'inskii O B, Kolosova L I, Lebedev V P, Avelev V D and Petrova O G. Effects of transcranial electrical stimulation of opioid brain structures on regeneration of peripheral nerves in the rat. Neurophysiology 1990; 22(1):76-79.

100. Enin L D, Akoev G N, Lebedev V P and Potekhina I L. Skin mechanoreceptor function in albino rats during transcranial electrical stimulation. Bull Exp Biol Med 1990; 110(5): 1462-4.

101. Enin L D, Akoev G N, Lebedev V P and Potekhina I L. Altered excitability of rat cutaneous mechanoreceptors during transcranial electrical stimulation. Neurophysiology 1990; 22 (4): 367-71.

102. Tan G, Rintala D H, Thornby J I, Yang J, Wade W, and Vasilev C: Using cranial electrotherapy stimulation to treat pain associated with spinal cord injury. J Rehabil Res Dev 2006; 43(4): 461-74.

103. Lichtbroun A S, Raicer M M, and Smith R B: The treatment of fibromyalgia with cranial electrotherapy stimulation. J Clin Rheumatol 2001; 7(2): 72-8.

104. Kirsch D L, Smith R B: The use of cranial electrotherapy stimulation in the management of chronic pain: A review. NeuroRehabilitation 2000; 14(2): 85-94.

105. Fregni F, Boggio P S, Lima M C, Ferreira M J, Wagner T, Rigonatti S P, Castro A W, Souza D R, Riberto M, Freedman S D, Nitsche M A, and Pascual-Leone A: A sham-controlled, phase II trial of transcranial direct current stimulation for the treatment of central pain in traumatic spinal cord injury. Pain 2006; 122: 197-209.

106. Fregni F, Gimenes R, Valle A C, Ferreira M J, Rocha R R, Natalle L, Bravo R, Rigonatti S P, Freedman S D, Nitsche M A, Pascual-Leone A, and Boggio P S: A randomized, sham-controlled, proof of principle study of transcranial direct current stimulation for the treatment of pain in fibromyalgia. Arthritis Rheum 2006; 54: 3988-3998.

107. Boggio P S, Zaghi S, Lopes M, and Fregni F: Modulatory effects of anodal transcranial direct current stimula- 107. [continued] tion on perception and pain thresholds in healthy volunteers. Eur J Neurol 2008; 15(10): 1124-30. Epub 2008 Aug. 20.
108. Cecilio S B, Zaghi S, Cecilio L B, Correa C F, and Fregni F: Exploring a novel therapeutic approach with noninvasive cortical stimulation for vulvodynia. Am J Obstet Gynecol 2008; 199(6): e6-7.
109. Imamura M, Imamura S T, Kaziyama H H, Targino R A, Hsing W T, de Souza L P, Cutait M M, Fregni F, and Camanho G L: Impact of nervous system hyperalgesia on pain, disability, and quality of life in patients with knee osteoarthritis: a controlled analysis. Arthritis Rheum 2008; 59(10): 1424-31.
110. Lima M C, Fregni F: Motor cortex stimulation for chronic pain: systematic review and meta-analysis of the literature. Neurology 2008; 70(24): 2329-37.
111. Silva G, Miksad R, Freedman S D, Pascual-Leone A, Jain S, Gomes D L, Amancio E J, Boggio P S, Correa C F, and Fregni F: Treatment of cancer pain with noninvasive brain stimulation. J Pain Symptom Manage 2007; 34(4): 342-5.
112. Jensen M P, Hakimian S, Sherlin L H, and Fregni F: New insights into neuromodulatory approaches for the treatment of pain. J Pain 2008; 9(3): 193-9. Epub 2007 Dec. 21.
113. Patrizi F, Freedman S D, Pascual-Leone A, and Fregni F: Novel therapeutic approaches to the treatment of chronic abdominal visceral pain. ScientificWorldJournal 2006; 6: 472-90.
114. Fregni F, DaSilva D, Potvin K, Ramos-Estebanez C, Cohen D, Pascual-Leone A, and Freedman S D: Treatment of chronic visceral pain with brain stimulation Ann Neurol 2005; 58(6): 971-2.
115. Liss S, Liss B: Physiological and therapeutic effects of high frequency electrical pulses. Integr Physiol Behav Sci 1996; 31: 88-95.
116. Boggio P S, Carreiro L R, and Fregni F: Cortical stimulation with weak electrical currents for cognitive modulation in attention deficit hyperactivity disorder. Med Hypotheses 2009; 72(5): 613-4.
117. Ferrucci R, Mameli F, Guidi I, Mrakic-Sposta S, Vergari M, Marceglia S, Cogiamanian F, Barbieri S, Scarpini E, and Priori A: Transcranial direct current stimulation improves recognition memory in Alzheimer disease. Neurology 2008; 71(7): 493-8.
118. Boggio P S, Khoury L P, Martins D C, Martins O E, de Macedo E C, and Fregni F: Temporal cortex direct current stimulation enhances performance on a visual recognition memory task in Alzheimer disease. J Neurol Neurosurg Psychiatry 2009; 80(4): 444-7. Epub 2008 Oct. 31.
119. Fregni F, Boggio P S, Nitsche M A, Rigonatti S P, and Pascual-Leone A: Cognitive effects of repeated sessions of transcranial direct current stimulation in patients with depression. Depress Anxiety 2006; 23(8): 482-4.
120. Boggio P S, Ferrucci R, Rigonatti S P, Covre P, Nitsche M, Pascual-Leone A, and Fregni F: Effects of transcranial direct current stimulation on working memory in patients with Parkinson's disease. J Neurol Sci 2006; 249(1): 31-8. Epub 2006 Jul. 14.
121. Fregni F, Boggio P S, Nitsche M, Bermpohl F, Antal A, Feredoes E, Marcolin M A, Rigonatti S P, Silva M T, Paulus W, and Pascual-Leone A: Anodal transcranial direct current stimulation of prefrontal cortex enhances working memory. Exp Brain Res 2005; 166(1): 23-30. Epub 2005 Jul. 6.
122. Alling F A, Johnson B D, Elmoghazy E: Cranial electrostimulation (CES) use in the detoxification of opiate-dependent patients. J Subst Abuse Treat 1990; 7:173-80.
123. Krupitski E M, Burakov A M, Karandashova G F, Katsnel'son IaS, Lebedev V P, Grinenko A J, and Borodkin J S: The administration of transcranial electrical treatment for affective disturbances therapy in alcoholic patients. Drug Alcohol Depend 1991; 27(1):1-6.
124. Bystritsky A, Kerwin L, and Feusner J: A pilot study of cranial electrotherapy stimulation for generalized anxiety disorder. J Clin Psychiatry 2008; 69(3): 412-7.
125. Liss S, Liss B: Physiological and therapeutic effects of high frequency electrical pulses. Integr Physiol Behav Sci 1996; 31: 88-95.
126. Boggio P, Zaghi S, and Fregni F: Modulation of emotions associated with images of human pain using anodal transcranial stimulation (tDC). Neuropsychologia 2009; 47: 212-7.
127. Ferrucci R, Bortolomasi M, Vergari M, Tadini L, Salvoro B, Giacopuzzi M, Barbieri S, and Priori A: Transcranial direct current stimulation in severe, drug-resistant major depression. J Affect Disord 2009; doi:10.1016/j.jad.2009.02.015 [Epub ahead of print].
128. Nitsche M A, Boggio P S, Fregni F, and Pascual-Leone A: Treatment of depression with transcranial direct current stimulation (tDCS): A Review. Exp Neurol 2009; doi: 10.1016/j.expneurol.2009.03.038 [Epub ahead of print].
129. Boggio P S, Fregni F, Valasek C, Ellwood S, Chi R, Gallate J, Pascual-Leone A, and Snyder A: Temporal lobe cortical electrical stimulation during the encoding and retrieval phase reduces false memories. PLoS ONE 2009; 4(3): e4959. Epub 2009 Mar. 25.
130. Murphy D N, Boggio P, and Fregni F: Transcranial direct current stimulation as a therapeutic tool for the treatment of major depression: insights from past and recent clinical studies. Curr Opin Psychiatry 2009; 22(3): 306-11.
131. Brunoni A R, Lopes M, Kaptchuk T J, and Fregni F: Placebo response of non-pharmacological and pharmacological trials in major depression: a systematic review and meta-analysis. PLoS ONE 2009; 4(3): e4824. Epub 2009 Mar. 18.
132. Boggio P S, Rigonatti S P, Ribeiro R B, Myczkowski M L, Nitsche M A, Pascual-Leone A, and Fregni F: A randomized, double-blind clinical trial on the efficacy of cortical direct current stimulation for the treatment of major depression. Int J Neuropsychopharmacol 2008; 11(2): 249-54. Epub 2007 Jun. 11.
133. Bajwa S, Bermpohl F, Rigonatti S P, Pascual-Leone A, Boggio P S, and Fregni F: Impaired interhemispheric interactions in patients with major depression. J Nerv Ment Dis 2008; 196(9): 671-7
134. Rigonatti S P, Boggio P S, Myczkowski M L, Otta E, Fiquer J T, Ribeiro R B, Nitsche M A, Pascual-Leone A, and Fregni F: Transcranial direct stimulation and fluoxetine for the treatment of depression. Eur Psychiatry 2008; 23(1): 74-6. Epub 2007 Nov. 19.
135. Brunoni A R, Lopes M, and Fregni F: A systematic review and meta-analysis of clinical studies on major depression and BDNF levels: implications for the role of neuroplasticity in depression. Int J Neuropsychopharmacol 2008; 11(8): 1169-80. Epub 2008 Aug. 28.
136. Bermpohl F, Pascual-Leone A, Amedi A, Merabet L B, Fregni F, Gaab N, Alsop D, Schlaug G, and Northoff G: Dissociable networks for the expectancy and perception of emotional stimuli in the human brain. Neuroimage 2006; 30(2): 588-600. Epub 2005 Nov. 7.
137. Boggio P S, Bermpohl F, Vergara A O, Muniz A L, Nahas F H, Leme P B, Rigonatti S P, and Fregni F: Go-no-go task performance improvement after anodal transcranial DC stimulation of the left dorsolateral prefrontal cortex in major depression. J Affect Disord 2007; 101(1-3): 91-8. Epub 2006 Dec. 12.
138. Boggio P S, Sultani N, Fecteau S, Merabet L, Mecca T, Pascual-Leone A, Basaglia A, and Fregni F: Prefrontal cortex modulation using transcranial DC stimulation reduces alcohol craving: a double-blind, sham-controlled study. Drug Alcohol Depend 2008; 92(1-3): 55-60. Epub 2007 Jul. 19.
139. Fecteau S, Pascual-Leone A, Zald D H, Liguori P, Théoret H, Boggio P S, and Fregni F: Activation of prefrontal cortex by transcranial direct current stimulation reduces appetite for risk during ambiguous decision making. J Neurosci 2007; 27(23): 6212-8.
140. Sharova E V, Mel'nikov A V, Novikova M R, Kulikov M A, Grechenko T N, Shekhter E D, and Zaslayskii A Yu: Changes in spontaneous brain bioelectrical activity during transcranial electrical and electromagnetic stimulation. Neurosci and Behav Physiol 2007; 37(5): 451-7.
141. Wu A D, Fregni F, Simon D K, Deblieck C, and Pascual-Leone A: Noninvasive brain stimulation for Parkinson's disease and dystonia. Neurotherapeutics 2008; 5(2):345-61.
142. Boggio P S, Nunes A, Rigonatti S P, Nitsche M A, Pascual-Leone A, and Fregni F: Repeated sessions of non-invasive brain DC stimulation is associated with motor function improvement in stroke patients. Restor Neurol Neurosci 2007; 25: 123-129.
143. Hesse S, Werner C, Schonhardt E M, Bardeleben A, Jenrich W, and Kirker S G: Combined transcranial direct current stimulation and robot-assisted arm training in sub-acute stroke patients: a pilot study. Restor Neurol Neurosci 2007; 25: 9-15.
144. Fregni F, Boggio P S, Santos M C, Lima M, Vieira A L, Rigonatti S P, Silva M T, Barbosa E R, Nitsche M A, and Pascual-Leone A: Noninvasive cortical stimulation with transcranial direct current stimulation in Parkinson's disease. Mov Disord 2006; 21(10): 1693-702.
145. Nielsen L A, Curatolo M, and Drewes A: Human experimental pain models in drug development: Translational pain research. Curr Opin Investig Drugs 2007; 8(1): 41-53.
146. Staahl C, Drewes A M: Experimental Human Pain Models: A review of standardised methods for preclinical testing of analgesics. Basic Clin Pharmacol Toxicol 2004; 95: 97-111.
147. Angst M S, Ramaswamy B, Riley E T, et al. Lumbar epidural morphine in humans and supraspinal analgesia to experimental heat pain. Anesthesiology 2000; 92:312-24. [see comments]. Angst M S, Drover D R, Lotsch J, et al. Pharmacodynamics of orally administered sustained-release hydromorphone in humans. Anesthesiology 2001; 94:63-73.
148. Angst M S, Koppert W, Pahl I, et al. Short-term infusion of the muopioid agonist remifentanil in humans causes hyperalgesia during withdrawal. Pain 2003; 106:49-57.
149. Angst M S, Ramaswamy B, Davis M F, et al. Comparative analgesic and mental effects of increasing plasma concentrations of dexmedetomidine and alfentanil in humans. Anesthesiology 2004; 101:744-52.
150. Enggaard T P, Poulsen L, Arendt-Nielsen L, et al. The analgesic effect of codeine as compared to imipramine in different human experimental pain models. Pain 2001; 92:277-82.
151. Koltzenburg M, Pokorny R, Gasser U E, et al. Differential sensitivity of three experimental pain models in detecting the analgesic effects of transdermal fentanyl and buprenorphine. Pain 2006.
152. Lotsch J, Angst M S. The mu-opioid agonist remifentanil attenuates hyperalgesia evoked by blunt and punctuated stimuli with different potency: a pharmacological evaluation of the freeze lesion in humans. Pain 2003; 102:151-61.
153. Luginbuhl M, Schnider T W, Petersen-Felix S, et al. Comparison of five experimental pain tests to measure analgesic effects of alfentanil. Anesthesiology 2001; 95:22-9.
154. Auriacombe M, Tignol J, Le Moal M, and Stinus L: Transcutaneous electrical stimulation with Limoge current potentiates morphine analgesia and attenuates opiate abstinence syndrome. Biological Psychiatry 1990; 28(8):650-6.
155. Malin D H, Lake J R, Hamilton R F, and Skolnick M H: Augmented analgesic effects of enkephalinase inhibitors combined with transcranial electrostimulation. Life Sci 1989; 44:1371-6.
156. Siegesmund K A, Sances A Jr, and Larson S J: Effects of electroanesthesia on synaptic ultrastructure. J Neurol Sci 1969; 9:89-96.
157. Lebedev V P, Ilynsky O B, Savchenko A B, Kolosova L L, Kovalevskii A V, Tsirulnikov E M, Rychkova S V, Melikhova M V, Aleksandrov V A, Gerasimova L I, and Pavlov V A: Noninvasive transcranial electrostimulation of the endorphin structures of the brain as a reparation activator: experimental and clinical parallels. Biomed Eng 2002; 36(6): 335-8
158. Lebedev V P, Bilichenko S V, Ordyan N E, Pivina S G, Nechiporenko S P, Puzyrev A A, Mikheeva E A, and Kubacheva K K: Transcranial electrostimulation activates reparative regeneration and the insulin-producing function of pancreatic B-cells in alloxan diabetes rats. Neurosci Behav Physiol 2007; 37(4): 204-13.
159. Banich M T, et al., Neurosci Biobehav Rev 2009; 33(5): 613-30.
160. Kopp C; et al., Neuropharmacology 2007; 53(1):1-9.

What is claimed is:

1. A method for administering transcranial electrical stimulation (TES) for treating or preventing a medical condition in a human subject, comprising:
 a) removably fixing a frontal electrode on the frontal area of the head positioned on the subject's forehead covering an area inferiorly approximately at the level of the eyebrows and extending superiorly approximately to the hair line along the lateral part of the orbit;
 and a posterior pair of electrodes positioned on the back of the head at positions selected from the group consisting of:
  1. an area bordered (a) on the outside by the mastoid process; (b) on the inside to about 2 cm medial to the external occipital protuberance; (c) inferiorly by the intermastoid line; and superiorly to at least 1 cm above the external occipital protuberance;
  2. an area from about 1.5 to about 4 cm lateral to an external occipital protuberance (EOP) to about 2 cm superior to intermastoid (IM) line or as low as about 1 cm below the IM line, and to about 0.5 cm superior to EOP;
  3. an area from about 5-7 cm lateral to an external occipital protuberance (EOP) either at the intermastoid (IM) line or above it, to about the midpoint between the EOP and IM lines or to below the superior nuchal line; and
  4. an area from about 9 cm lateral to EOP to about 1 cm above the mastoid tip;
 b) supplying electrical current to the frontal electrode and to the pair of second electrodes for a period of time to elicit a response from the subject, wherein 1. the electrical current comprises AC current pulses superimposed on direct current, AC current pulses alone or DC current alone, and
2. the current pulses are supplied at a particular frequency of between from about 10 Hz to about 100 Hz.

2. The method of claim 1, wherein the AC current pulses have a shape selected from the group comprising rectangular, sinusoidal, triangular, saw-shaped and other custom shaped pulses.

3. The method of claim 1, wherein the AC current is unipolar or bipolar.

4. The method of claim 1, wherein the AC current pulses comprise modulate high frequency AC current pulses of frequency from about 1 kHz to about 10 MHz are modulated by the pulses.

5. The method of claim 1, wherein the total current value supplied is from about 0.2 mA and about 20 mA.

6. The method of claim 5, wherein the total current value is a sum of the direct current and either a Mean Absolute Deviation (MAD) or root-mean-square (RMS) value of the current pulses.

7. The method of claim 6, wherein the electric current is AC current pulses superimposed on DC current, and a ratio between the value of the direct current and the Mean Absolute Deviation (MAD) value of the current pulses is between from about 5:1 and from about 1:1.

8. The method of claim 1, wherein the ratio between the value of the direct current and the Mean Absolute Deviation (MAD) value of the current pulses is about 2:1.

9. The method of claim 1, wherein the polarity of the AC current pulses superimposed on direct current, AC current pulses alone or DC current alone is changed during the TES.

10. The method of claim 1, wherein the wave form of the current is changed during TES.

11. The method of claim 1, wherein a duration of each AC current pulse is below about 8 msec, preferably about 3.5 msec.

12. The method of claim 1, wherein the duration of the AC current pulse is changed during TES.

13. The TES method of claim 1, wherein the frontal electrode is removably fixed to the skin of the subject's forehead above the eyebrows and the pair of second electrodes is removably fixed to the skin in the retromastoid and occipital areas.

14. The method of claim 1, wherein the electric current is supplied for a period of from about 10 minutes to about 60 minutes.

15. The method of claim 1, wherein the medical condition is selected from the group comprising acute and chronic pain conditions and syndromes; immune system dysfunction and disorders; decreased wound healing; tissue and nerve regeneration disorders; impaired neurological function; and drug dependence and withdrawal.

16. The method of claim 1, wherein the medical condition is selected from the group comprising attention deficit disorder, anxiety, depression, mood and sleep disturbances, post-traumatic stress disorder, appetite disturbances, Alzheimer's disease, neurodegenerative diseases including Parkinson's disease, sexual dysfunction, fatigue, combat stress, and improving neurocognitive and mood performance.

17. The method of claim 1, wherein the duration of each AC current pulse is about 3.5 msec.

18. The method of claim 1, wherein the particular frequency is above 65 Hz.

19. The method of claim 1, wherein the particular frequency is held constant during the transcranial electrical stimulation (TES).

20. The method of claim 1, wherein the particular frequency is between about 30 Hz and about 65 Hz.

21. The method of claim 1, wherein the particular frequency is about 60 Hz.

* * * * *